(12) United States Patent
Sales et al.

(10) Patent No.: US 10,307,085 B2
(45) Date of Patent: Jun. 4, 2019

(54) WEARABLE PHYSIOLOGY MONITOR COMPUTER APPARATUS, SYSTEMS, AND RELATED METHODS

(71) Applicant: Vision Service Plan, Rancho Cordova, CA (US)

(72) Inventors: Jay William Sales, Citrus Heights, CA (US); Richard Chester Klosinski, Jr., Sacramento, CA (US); Matthew Allen Workman, Sacramento, CA (US); Meghan Kathleen Murphy, Davis, CA (US); Matthew David Steen, Sacramento, CA (US)

(73) Assignee: Vision Service Plan, Rancho Cordova, CA (US)

( * ) Notice: Subject to any disclaimer, the term of this patent is extended or adjusted under 35 U.S.C. 154(b) by 778 days.

(21) Appl. No.: 14/610,439

(22) Filed: Jan. 30, 2015

(65) Prior Publication Data

US 2016/0066847 A1    Mar. 10, 2016

Related U.S. Application Data

(60) Provisional application No. 62/046,406, filed on Sep. 5, 2014.

(51) Int. Cl.
  *A61B 5/00* (2006.01)
  *A61B 5/1455* (2006.01)
  (Continued)

(52) U.S. Cl.
  CPC .............. *A61B 5/112* (2013.01); *A61B 3/112* (2013.01); *A61B 5/0002* (2013.01);
  (Continued)

(58) Field of Classification Search
  CPC ..... A61B 5/1455; A61B 5/112; A61B 5/6803; A61B 5/0002; A61B 5/165; A61B 5/4076;
  (Continued)

(56) References Cited

U.S. PATENT DOCUMENTS 3,505,879 A    4/1970  Vanderberg
3,548,663 A    12/1970 Radin
(Continued)

FOREIGN PATENT DOCUMENTS

EP    2778612    12/2017
GB    2396421    6/2004
(Continued)

OTHER PUBLICATIONS

Final Office Action, dated Dec. 15, 2016, from corresponding U.S. Appl. No. 14/506,249.
(Continued)

*Primary Examiner* — Eric F Winakur
(74) *Attorney, Agent, or Firm* — Brient IP Law, LLC

(57) ABSTRACT

A computer-implemented method of detecting physiological attributes of a wearer of a computerized wearable device having one or more sensors comprises (1) using the information from the one or more sensors to assess the physiology of the wearer; and (2) notifying the wearer of the wearer's physiology. In various embodiments, the method involves using the wearable device to determine the wearer's current posture, balance, alertness, and/or physical state and comparing the current posture, balance, alertness and/or physical state to at least one baseline measurement. For example, the system may measure a baseline posture to determine when the wearer's current posture deviates from the baseline posture, and notify the wearer so that the wearer may improve his or her posture. In other embodiments, the
(Continued)

computerized wearable device may detect one or more of the wearer's physiological characteristics (e.g., oxygen levels, pulse rate, pupil size, etc.) and determine the wearer's alertness level.

18 Claims, 4 Drawing Sheets

(51) Int. Cl.

| | | |
|---|---|---|
| A61B 5/16 | (2006.01) | |
| A61B 5/11 | (2006.01) | |
| A61B 3/11 | (2006.01) | |
| A61B 5/0402 | (2006.01) | |
| A61B 5/0476 | (2006.01) | |
| A61B 5/103 | (2006.01) | |
| A61B 5/1171 | (2016.01) | |
| A61B 7/04 | (2006.01) | |
| G09B 5/00 | (2006.01) | |
| G06K 9/00 | (2006.01) | |
| G06K 9/62 | (2006.01) | |
| G08B 21/04 | (2006.01) | |
| A63B 24/00 | (2006.01) | |
| G09B 5/06 | (2006.01) | |
| G09B 19/00 | (2006.01) | |
| G06F 19/00 | (2018.01) | |
| G06F 21/35 | (2013.01) | |
| G07C 9/00 | (2006.01) | |
| G08B 21/02 | (2006.01) | |
| H04L 29/06 | (2006.01) | |
| G16H 40/63 | (2018.01) | |
| G16H 50/20 | (2018.01) | |
| A61B 5/117 | (2016.01) | |
| A61F 2/76 | (2006.01) | |
| A61B 5/0205 | (2006.01) | |
| A61B 5/024 | (2006.01) | |
| A61B 5/053 | (2006.01) | |
| A61B 5/08 | (2006.01) | |
| G02C 11/00 | (2006.01) | |

(52) U.S. Cl.
CPC .......... *A61B 5/0022* (2013.01); *A61B 5/0077* (2013.01); *A61B 5/0402* (2013.01); *A61B 5/0476* (2013.01); *A61B 5/1032* (2013.01); *A61B 5/1103* (2013.01); *A61B 5/117* (2013.01); *A61B 5/1114* (2013.01); *A61B 5/1116* (2013.01); *A61B 5/1128* (2013.01); *A61B 5/1176* (2013.01); *A61B 5/14552* (2013.01); *A61B 5/165* (2013.01); *A61B 5/4076* (2013.01); *A61B 5/4266* (2013.01); *A61B 5/443* (2013.01); *A61B 5/486* (2013.01); *A61B 5/4884* (2013.01); *A61B 5/6803* (2013.01); *A61B 5/7246* (2013.01); *A61B 5/7278* (2013.01); *A61B 7/04* (2013.01); *A63B 24/0062* (2013.01); *G06F 19/00* (2013.01); *G06F 19/3481* (2013.01); *G06F 21/35* (2013.01); *G06K 9/00348* (2013.01); *G06K 9/00597* (2013.01); *G06K 9/00604* (2013.01); *G06K 9/00617* (2013.01); *G06K 9/00664* (2013.01); *G06K 9/6201* (2013.01); *G07C 9/00158* (2013.01); *G08B 21/02* (2013.01); *G08B 21/0423* (2013.01); *G08B 21/0461* (2013.01); *G08B 21/0476* (2013.01); *G09B 5/00* (2013.01); *G09B 5/06* (2013.01); *G09B 19/0092* (2013.01); *G16H 40/63* (2018.01); *G16H 50/20* (2018.01); *H04L 63/0861* (2013.01); *A61B 5/024* (2013.01); *A61B 5/0205* (2013.01); *A61B 5/0531* (2013.01); *A61B 5/0816* (2013.01); *A61B 5/1118* (2013.01); *A61B 5/7282* (2013.01); *A61B 2560/0475* (2013.01); *A61B 2562/0219* (2013.01); *A61B 2562/0223* (2013.01); *A61B 2562/0257* (2013.01); *A61B 2576/00* (2013.01); *A61F 2/76* (2013.01); *A61F 2002/7695* (2013.01); *G02C 11/10* (2013.01)

(58) Field of Classification Search
CPC ..... A61B 5/486; A61B 5/4884; A61B 5/7246; A61B 5/7278; A61B 5/1116; A61B 5/14552

See application file for complete search history.

(56) References Cited

U.S. PATENT DOCUMENTS

| | | |
|---|---|---|
| 3,972,038 A | 7/1976 | Fletcher et al. |
| 4,100,401 A | 7/1978 | Tutt et al. |
| 4,186,609 A | 2/1980 | Baermann |
| 4,195,642 A | 4/1980 | Price et al. |
| 4,281,663 A | 8/1981 | Pringle |
| 4,407,295 A | 10/1983 | Steuer et al. |
| 4,434,801 A | 3/1984 | Jiminez et al. |
| 4,855,942 A | 8/1989 | Bianco |
| 4,878,749 A | 11/1989 | McGee |
| 4,919,530 A | 4/1990 | Hyman |
| 5,422,816 A | 6/1995 | Sprague et al. |
| 5,452,480 A | 9/1995 | Ryden |
| 5,497,143 A | 3/1996 | Matsuo et al. |
| 5,585,871 A | 12/1996 | Linden |
| 5,670,872 A | 9/1997 | Van De Walle et al. |
| 5,746,501 A | 5/1998 | Chien et al. |
| 5,891,042 A | 4/1999 | Sham et al. |
| 5,931,764 A | 8/1999 | Freeman et al. |
| 5,966,680 A | 10/1999 | Butnaru |
| 5,976,083 A | 11/1999 | Richardson et al. |
| 6,013,007 A | 1/2000 | Root et al. |
| 6,183,425 B1 | 2/2001 | Whalen et al. |
| 6,218,958 B1 | 4/2001 | Eichstaedt et al. |
| 6,241,684 B1 | 6/2001 | Amano et al. |
| 6,325,507 B1 | 12/2001 | Jannard et al. |
| 6,381,482 B1 | 4/2002 | Jayaraman et al. |
| 6,431,705 B1 | 8/2002 | Linden et al. |
| 6,439,067 B1 | 8/2002 | Goldman et al. |
| 6,513,532 B2 | 2/2003 | Mault et al. |
| 6,532,298 B1 | 3/2003 | Cambier et al. |
| 6,736,759 B1 | 5/2004 | Stubbs et al. |
| 6,769,767 B2 | 8/2004 | Swab et al. |
| 6,783,501 B2 | 8/2004 | Takahashi et al. |
| 6,790,178 B1 | 9/2004 | Mault et al. |
| 6,812,845 B2 | 11/2004 | Yuzuki et al. |
| 7,181,345 B2 | 2/2007 | Rosenfeld et al. |
| 7,187,960 B2 | 3/2007 | Abreu |
| 7,192,136 B2 | 3/2007 | Howell et al. |
| 7,255,437 B2 | 8/2007 | Howell et al. |
| 7,376,238 B1 | 5/2008 | Rivas et al. |
| 7,380,936 B2 | 6/2008 | Howell et al. |
| 7,400,257 B2 | 7/2008 | Rivas |
| 7,401,918 B2 | 7/2008 | Howell et al. |
| 7,438,410 B1 | 10/2008 | Howell et al. |
| 7,454,002 B1 | 11/2008 | Gardner et al. |
| 7,457,434 B2 | 11/2008 | Azar |
| 7,481,531 B2 | 1/2009 | Howell et al. |
| 7,488,294 B2 | 2/2009 | Torch |
| 7,500,746 B1 | 3/2009 | Howell et al. |
| 7,500,747 B2 | 3/2009 | Howell et al. |
| 7,515,054 B2 | 4/2009 | Torch |
| 7,543,934 B2 | 6/2009 | Howell et al. |
| 7,581,833 B2 | 9/2009 | Howell et al. |
| 7,621,634 B2 | 11/2009 | Howell et al. |
| 7,630,524 B2 | 12/2009 | Lauper et al. |
| 7,634,379 B2 | 12/2009 | Noble |
| 7,640,135 B2 | 12/2009 | Vock et al. |

(56) References Cited

U.S. PATENT DOCUMENTS

| | | |
|---|---|---|
| 7,648,463 B1 | 1/2010 | Elhag et al. |
| 7,677,723 B2 | 3/2010 | Howell et al. |
| 7,771,046 B2 | 8/2010 | Howell et al. |
| 7,792,552 B2 | 9/2010 | Thomas et al. |
| 7,793,361 B2 | 9/2010 | Ishihara et al. |
| 7,857,772 B2 | 9/2010 | Bouvier et al. |
| 7,806,525 B2 | 10/2010 | Howell et al. |
| 7,922,321 B2 | 4/2011 | Howell et al. |
| 7,987,070 B2 | 7/2011 | Kahn et al. |
| 8,007,450 B2 | 8/2011 | Williams |
| 8,011,242 B2 | 9/2011 | O'Neill et al. |
| 8,081,082 B2 | 12/2011 | Malik et al. |
| 8,109,629 B2 | 2/2012 | Howell et al. |
| 8,157,730 B2 | 4/2012 | Leboeuf et al. |
| 8,188,868 B2 | 5/2012 | Case |
| 8,202,148 B2 | 6/2012 | Young |
| 8,294,581 B2 | 10/2012 | Kamen |
| 8,303,311 B2 | 11/2012 | Forest |
| 8,337,013 B2 | 12/2012 | Howell et al. |
| 8,384,617 B2 | 2/2013 | Braun et al. |
| 8,430,507 B2 | 4/2013 | Howell et al. |
| 8,448,846 B2 | 5/2013 | Needhan et al. |
| 8,449,471 B2 | 5/2013 | Tran |
| 8,465,151 B2 | 6/2013 | Howell et al. |
| 8,494,507 B1 | 7/2013 | Tedesco et al. |
| 8,500,271 B2 | 8/2013 | Howell et al. |
| 8,510,166 B2 | 8/2013 | Neven |
| 8,531,355 B2 | 9/2013 | Maltz |
| 8,540,583 B2 | 9/2013 | Leech |
| 8,568,313 B2 | 10/2013 | Sadhu |
| 8,594,971 B2 | 11/2013 | Keal et al. |
| 8,620,600 B2 | 12/2013 | Vock et al. |
| 8,630,633 B1 | 1/2014 | Tedesco et al. |
| 8,634,701 B2 | 1/2014 | Kang et al. |
| 8,647,270 B2 | 2/2014 | Leboeuf et al. |
| 8,690,750 B2 | 4/2014 | Krueger |
| 8,696,113 B2 | 4/2014 | Lewis |
| 8,733,928 B1 | 5/2014 | Lewis |
| 8,750,971 B2 | 6/2014 | Tran |
| 8,764,651 B2 | 7/2014 | Tran |
| 8,849,610 B2 | 9/2014 | Molettiere et al. |
| 8,892,401 B2 | 11/2014 | Yuen et al. |
| 8,905,542 B2 | 12/2014 | Howell et al. |
| 8,911,087 B2 | 12/2014 | Publicover et al. |
| 8,920,332 B2 | 12/2014 | Hong et al. |
| 8,931,896 B2 | 1/2015 | Blum et al. |
| 8,941,560 B2 | 1/2015 | Wong et al. |
| 8,944,590 B2 | 2/2015 | Blum et al. |
| 8,961,415 B2 | 2/2015 | Leboeuf et al. |
| 8,964,298 B2 | 2/2015 | Haddick et al. |
| 8,965,730 B2 | 2/2015 | Yuen |
| 8,979,295 B2 | 2/2015 | Waters |
| 9,001,427 B2 | 4/2015 | Jacobs et al. |
| 9,005,129 B2 | 4/2015 | Venkatraman et al. |
| 9,007,220 B2 | 4/2015 | Johns et al. |
| 9,028,405 B2 | 5/2015 | Tran |
| 9,031,812 B2 | 5/2015 | Roberts et al. |
| 9,033,493 B2 | 5/2015 | Howell et al. |
| 9,035,970 B2 | 5/2015 | Lamb et al. |
| 9,050,033 B2 | 6/2015 | Yoneyama et al. |
| 9,064,342 B2 | 6/2015 | Yuen et al. |
| 9,112,701 B2 | 8/2015 | Sano et al. |
| 9,113,794 B2 | 8/2015 | Hong et al. |
| 9,113,795 B2 | 8/2015 | Hong et al. |
| 9,141,194 B1 | 9/2015 | Keyes et al. |
| 9,144,405 B2 | 9/2015 | Kim et al. |
| 9,153,074 B2 | 10/2015 | Zhou et al. |
| 9,215,290 B2 | 12/2015 | Yuen et al. |
| 9,235,064 B2 | 1/2016 | Lewis |
| 9,239,473 B2 | 1/2016 | Lewis |
| 9,241,635 B2 | 1/2016 | Yuen et al. |
| 9,244,293 B2 | 1/2016 | Lewis |
| 9,247,212 B2 | 1/2016 | Bose et al. |
| 9,254,100 B2 | 2/2016 | Beck et al. |
| 9,304,331 B2 | 4/2016 | Carrara |
| 9,341,526 B2 | 5/2016 | Bass et al. |
| 9,342,610 B2 | 5/2016 | Liu et al. |
| 9,480,877 B2 | 11/2016 | Chiang et al. |
| 9,520,638 B2 | 12/2016 | Baringer et al. |
| 9,529,197 B2 | 12/2016 | Olsson et al. |
| 9,566,033 B2 | 2/2017 | Bogdanovich et al. |
| 9,579,060 B1 | 2/2017 | Lisy et al. |
| 9,610,476 B1 | 4/2017 | Tran et al. |
| 9,726,904 B1 | 8/2017 | Lin |
| 9,763,592 B2 | 9/2017 | Le et al. |
| 9,896,154 B2 | 2/2018 | Modolo |
| 9,977,259 B2 | 5/2018 | Archambeau et al. |
| 10,188,323 B2 | 1/2019 | Sales et al. |
| 2001/0031031 A1 | 10/2001 | Ogawa et al. |
| 2002/0151810 A1 | 10/2002 | Wong et al. |
| 2003/0195398 A1 | 10/2003 | Suzuki et al. |
| 2004/0039517 A1 | 2/2004 | Biesinger et al. |
| 2005/0033200 A1 | 2/2005 | Soehren et al. |
| 2005/0036103 A1 | 2/2005 | Bloch |
| 2005/0054942 A1 | 3/2005 | Melker et al. |
| 2006/0115130 A1 | 6/2006 | Kozlay |
| 2007/0052672 A1 | 3/2007 | Ritter et al. |
| 2007/0112287 A1 | 5/2007 | Fancourt et al. |
| 2007/0273611 A1 | 11/2007 | Torch |
| 2008/0137916 A1 | 6/2008 | Lauper et al. |
| 2009/0030350 A1 | 1/2009 | Yang et al. |
| 2009/0195747 A1 | 8/2009 | Insua |
| 2009/0227853 A1 | 9/2009 | Wijesiriwardana |
| 2009/0267805 A1 | 10/2009 | Jin et al. |
| 2010/0042430 A1 | 2/2010 | Bartfeld |
| 2010/0045928 A1 | 2/2010 | Levy |
| 2010/0110368 A1 | 5/2010 | Chaum |
| 2010/0136508 A1 | 6/2010 | Zekhtser |
| 2010/0271587 A1 | 10/2010 | Pavlopoulos |
| 2010/0280336 A1 | 11/2010 | Giftakis et al. |
| 2010/0308999 A1 | 12/2010 | Chornenky |
| 2010/0332571 A1 | 12/2010 | Healey et al. |
| 2011/0169932 A1 | 7/2011 | Mula et al. |
| 2011/0221656 A1 | 9/2011 | Haddick et al. |
| 2011/0224505 A1 | 9/2011 | Sadhu |
| 2012/0021806 A1 | 1/2012 | Maltz |
| 2012/0029367 A1 | 2/2012 | Hobeika |
| 2012/0127423 A1 | 5/2012 | Blum et al. |
| 2012/0133885 A1 | 5/2012 | Howell et al. |
| 2012/0135384 A1 | 5/2012 | Nakao |
| 2012/0142443 A1 | 6/2012 | Savarese et al. |
| 2012/0169990 A1 | 7/2012 | Burnstein |
| 2012/0191016 A1 | 7/2012 | Jastram |
| 2012/0203310 A1 | 8/2012 | Pugh et al. |
| 2012/0206485 A1 | 8/2012 | Osterhout et al. |
| 2012/0310442 A1 | 12/2012 | Doutaz et al. |
| 2013/0009907 A1 | 1/2013 | Rosenberg et al. |
| 2013/0009993 A1* | 1/2013 | Horseman ........... G06F 19/3418 345/633 |
| 2013/0024022 A1 | 1/2013 | Bowers |
| 2013/0024211 A1 | 1/2013 | Monteforte et al. |
| 2013/0041590 A1 | 2/2013 | Burich et al. |
| 2013/0050258 A1 | 2/2013 | Liu et al. |
| 2013/0096397 A1 | 4/2013 | Kiso et al. |
| 2013/0138413 A1 | 5/2013 | Finch et al. |
| 2013/0157232 A1 | 6/2013 | Ehrenkranz |
| 2013/0242262 A1 | 9/2013 | Lewis |
| 2013/0274587 A1 | 10/2013 | Coza et al. |
| 2013/0274904 A1 | 10/2013 | Coza et al. |
| 2013/0307670 A1 | 11/2013 | Ramaci |
| 2013/0329183 A1 | 12/2013 | Blum et al. |
| 2013/0345168 A1 | 12/2013 | Kim et al. |
| 2014/0028456 A1 | 1/2014 | Sadhu |
| 2014/0031703 A1 | 1/2014 | Rayner et al. |
| 2014/0063242 A1 | 3/2014 | Hanina et al. |
| 2014/0073081 A1 | 3/2014 | Wang |
| 2014/0078049 A1 | 3/2014 | Parshionikar |
| 2014/0085190 A1 | 3/2014 | Erinjippurath et al. |
| 2014/0135593 A1 | 5/2014 | Jayalth et al. |
| 2014/0142459 A1 | 5/2014 | Jayalth et al. |
| 2014/0159862 A1 | 6/2014 | Yang et al. |
| 2014/0204334 A1 | 7/2014 | Stoll |
| 2014/0207264 A1 | 7/2014 | Quy |
| 2014/0218281 A1 | 8/2014 | Amayeh et al. |

(56) References Cited

U.S. PATENT DOCUMENTS

| | | |
|---|---|---|
| 2014/0228649 A1 | 8/2014 | Rayner et al. |
| 2014/0229220 A1 | 8/2014 | Yuen et al. |
| 2014/0247145 A1 | 9/2014 | Proud |
| 2014/0266988 A1 | 9/2014 | Fisher et al. |
| 2014/0276096 A1 | 9/2014 | Bonutti |
| 2014/0340221 A1 | 11/2014 | Yuen et al. |
| 2014/0346158 A1 | 11/2014 | Matthews |
| 2014/0375452 A1 | 12/2014 | Yuen et al. |
| 2014/0375470 A1 | 12/2014 | Malveaux |
| 2014/0378872 A1 | 12/2014 | Hong et al. |
| 2015/0057512 A1 | 2/2015 | Kapoor |
| 2015/0085245 A1 | 3/2015 | Howell et al. |
| 2015/0088464 A1 | 3/2015 | Yuen et al. |
| 2015/0173631 A1 | 6/2015 | Richards et al. |
| 2015/0179050 A1 | 6/2015 | Katingari et al. |
| 2015/0185506 A1 | 7/2015 | Lewis |
| 2015/0212329 A1 | 7/2015 | Sugihara et al. |
| 2015/0223805 A1 | 8/2015 | Whitman et al. |
| 2015/0244910 A1 | 8/2015 | Marston et al. |
| 2015/0281879 A1 | 10/2015 | Saadi |
| 2015/0287338 A1 | 10/2015 | Wells et al. |
| 2015/0332149 A1 | 11/2015 | Kolb et al. |
| 2015/0342482 A1 | 12/2015 | Carrara |
| 2015/0366518 A1 | 12/2015 | Sampson |
| 2016/0007849 A1 | 1/2016 | Krueger |
| 2016/0034042 A1 | 2/2016 | Joo |
| 2016/0041404 A1 | 2/2016 | Palermo et al. |
| 2016/0041613 A1 | 2/2016 | Klanner et al. |
| 2016/0117937 A1 | 4/2016 | Penders et al. |
| 2016/0314468 A1 | 10/2016 | Smith et al. |
| 2017/0323684 A1 | 11/2017 | Allen et al. |

FOREIGN PATENT DOCUMENTS

| | | |
|---|---|---|
| WO | 2005015163 | 2/2005 |
| WO | 2005094667 | 10/2005 |
| WO | 2007088374 | 8/2007 |
| WO | 2008073806 | 6/2008 |
| WO | 2010006370 | 1/2010 |
| WO | 2010062479 | 6/2010 |
| WO | 2010062481 | 6/2010 |
| WO | 2011086466 | 7/2011 |
| WO | 2012041485 | 4/2012 |
| WO | 2013188343 | 12/2013 |
| WO | 2014021602 | 2/2014 |
| WO | 2014108481 | 7/2014 |
| WO | 2014144918 | 9/2014 |
| WO | 2014144940 | 9/2014 |
| WO | 2014170280 | 10/2014 |
| WO | 2014188244 | 11/2014 |
| WO | 2015015025 | 2/2015 |
| WO | 2015081299 | 6/2015 |
| WO | 2015095924 | 7/2015 |
| WO | 2015127143 | 8/2015 |
| WO | 2015127441 | 8/2015 |
| WO | 2016017997 | 2/2016 |
| WO | 2016029803 | 3/2016 |

OTHER PUBLICATIONS

Final Office Action, dated Sep. 26, 2016, from corresponding U.S. Appl. No. 14/610,628.
International Search Report, dated Jan. 21, 2016, from corresponding International Application No. PCT/US2015/048612.
International Search Report, dated Jan. 21, 2016, from corresponding International Application No. PCT/US2015/048656.
International Search Report, dated Jun. 2, 2016, from corresponding International Application No. PCT/US2016/015705.
Invitation to Pay Additional Search Fees, dated Apr. 1, 2016, from corresponding International Application Serial No. PCT/US2016/015705.
Maria S. Redin, "Marathon Man", Article Jun. 15, 1998, MIT Media Laboratory.
Office Action, dated Aug. 19, 2016, from corresponding U.S. Appl. No. 14/578,039.
Office Action, dated Jul. 1, 2016, from corresponding U.S. Appl. No. 14/562,454.
Office Action, dated Jul. 22, 2016, from corresponding U.S. Appl. No. 14/506,249.
Office Action, dated Mar. 8, 2016, from corresponding U.S. Appl. No. 14/610,628.
Office Action, dated Sep. 2, 2016, from corresponding U.S. Appl. No. 14/588,122.
Restriction Requirement, dated Nov. 10, 2016, from corresponding U.S. Appl. No. 14/846,401.
Richard M. Satava, et al., "The Physiologic Cipher at Altitude: Telemedicine and Real-Time Monitoring of Climbers on Mount Everest", Telemedicine Journal and e-Health, vol. 6, No. 3, 2000, Mary Ann Liebert, Inc.
Written Opinion of the International Searching Authority, dated Jan. 21, 2016, from corresponding International Application No. PCT/US2015/048612.
Written Opinion of the International Searching Authority, dated Jan. 21, 2016, from corresponding International Application No. PCT/US2015/048656.
Written Opinion of the International Searching Authority, dated Jun. 2, 2016, from corresponding International Application No. PCT/US2016/015705.
Office Action, dated Dec. 29, 2016, from corresponding U.S. Appl. No. 14/610,589.
Phend, Crystal, "Calorie Intake Rises as Sleep Time Drops," Medpage Today, Medpage Today, LLC, Mar. 15, 2012, Web Dec. 19, 2016, http://www.medpagetoday.com/cardiology/prevention/31663.
Michael Franco, Tzoa wearable turns you into a walking air-quality sensor, Dec. 9, 2014, CNET, https://www.cnet.com/news/tzoa-wearable-turns-you-into-a-walking-air-quality-sensor/.
Notice of Allowance, dated Feb. 28, 2017, from corresponding U.S. Appl. No. 14/588,122.
Office Action, dated Feb. 10, 2017, from corresponding U.S. Appl. No. 14/846,401.
Office Action, dated Mar. 3, 2017, from corresponding U.S. Appl. No. 14/610,628.
Ted Burnham, Wearable Air Quality Sensor: Tzoa, Jan. 5, 2015, Postscapes, http://www.postscapes.com/wearable-air-quality-sensor-tzoa/.
Final Office Action, dated Mar. 29, 2017, from corresponding U.S. Appl. No. 14/562,454.
International Preliminary Report on Patentability, dated Mar. 16, 2017, from corresponding International Application No. PCT/US2015/048612.
International Preliminary Report on Patentability, dated Mar. 16, 2017, from corresponding International Application No. PCT/US2015/048656.
International Preliminary Report on Patentability, dated Mar. 16, 2017, from corresponding International Application No. PCT/US2015/048662.
Final Office Action, dated Jun. 30, 2017, from corresponding U.S. Appl. No. 14/610,589.
Bhankland, Stephen, "Google's electronic eyewear get 'Ok Glass' voice commands", Feb. 20, 2013, Cnet.com, https://www.cnet.com/news/googles-electronic-eyewear-gets-ok-glass-voice-commands/.
Office Action, dated Jun. 29, 2017, from corresponding U.S. Appl. No. 15/489,147.
Final Office Action, dated Jul. 10, 2017, from corresponding U.S. Appl. No. 14/846,401.
Final Office Action, dated May 23, 2017, from corresponding U.S. Appl. No. 14/578,039.
Notice of Allowance, dated Jun. 21, 2017, from corresponding U.S. Appl. No. 14/562,454.
Office Action, dated Jun. 27, 2017, from corresponding U.S. Appl. No. 15/060,333.
Tolentino, Mellisa, Udderly Clever Wearable Tech Solutions, http://siliconangle.com/blog/2014/03/25/udderly-clever-wearable-tech-solutions/, Mar. 25, 2014.

(56) References Cited

OTHER PUBLICATIONS

Torres, Juan Carlos, ODG R-7 Smart Glasses Carries Its Own Android Inside, http://androidcommunity.com/pdg-r-7-smart-glasses-carries-its-own-android-inside-20140919/, Sep. 19, 2014.
Office Action, dated Sep. 29, 2017, from corresponding U.S. Appl. No. 14/506,249.
Office Action, dated Sep. 26, 2017, from corresponding U.S. Appl. No. 14/846,401.
Notice of Allowance, dated Oct. 20, 2017, from corresponding U.S. Appl. No. 15/489,147.
Final Office Action, dated Nov. 16, 2017, from corresponding U.S. Appl. No. 14/610,628.
Office Action, dated Nov. 30, 2017, from corresponding U.S. Appl. No. 14/550,406.
Jeannet, Pierre-Yves, et al., "Continuous monitoring and quantification of multiple parameters of daily physical activity in ambulatory Duchenne muscular , dystrophy patients", Official Journal of the European Paediatric Neurology Society, 2011.
Notice of Allowance, dated Dec. 13, 2017, from corresponding U.S. Appl. No. 14/610,501.
Office Action, dated Jan. 11, 2018, from corresponding U.S. Appl. No. 15/074,679.
Invitation to Pay Additional Search Fees, dated Nov. 4, 2015, from corresponding International Application Serial No. PCT/US2015/048612.
Invitation to Pay Additional Search Fees, dated Nov. 4, 2015, from corresponding International Application Serial No. PCT/US2015/048656.
International Search Report, dated Dec. 18, 2015, from corresponding International Application No. PCT/US2015/048662.
Written Opinion of the International Searching Authority, dated Dec. 18, 2015, from corresponding International Application No. PCT/US2015/048662.
Office Action, dated Mar. 2, 2018, from corresponding U.S. Appl. No. 15/060,333.
Final Office Action, dated Mar. 30 2018, from corresponding U.S. Appl. No. 14/846,401.
Office Action, dated May 23, 2018, from corresponding U.S. Appl. No. 14/578,039.
Office Action, dated Jun. 8, 2018, from corresponding U.S. Appl. No. 14/610,501.
Final Office Action, dated Jun. 14, 2018, from corresponding U.S. Appl. No. 15/074,679.
Office Action, dated Aug. 7, 2018, from corresponding U.S. Appl. No. 14/550,406.
Final Office Action, dated Dec. 31, 2018, from corresponding U.S. Appl. No. 14/550,406.
Notice of Allowance, dated Sep. 13, 2018, from corresponding U.S. Appl. No. 15/594,898.
Office Action, dated Sep. 11, 2018, from corresponding U.S. Appl. No. 15/060,333.
Office Action, dated Oct. 4, 2018, from corresponding U.S. Appl. No. 15/791,196.
Notice of Allowance, dated Oct. 11, 2018, from corresponding U.S. Appl. No. 15/074,679.
Office Action, dated Dec. 11, 2018, from corresponding U.S. Appl. No. 14/610,501.
Final Office Action, dated Jan. 14, 2019, from corresponding U.S. Appl. No. 14/578,039.
Final Office Action, dated Jan. 14, 2019, from corresponding U.S. Appl. No. 15/060,333.
Office Action, dated Feb. 11, 2019, from corresponding U.S. Appl. No. 14/846,401.
Office Action, dated Mar. 21, 2019, from corresponding U.S. Appl. No. 16/259,646.
Office Action, dated Apr. 4, 2019, from corresponding U.S. Appl. No. 16/284,615.

* cited by examiner

WEARABLE PHYSIOLOGY MONITOR COMPUTER APPARATUS, SYSTEMS, AND RELATED METHODS

CROSS-REFERENCE TO RELATED APPLICATION

This application claims the benefit of U.S. Provisional Patent Application No. 62/046,406, filed Sep. 5, 2014, and entitled, "Wearable Health Computer Apparatus, Systems, and Related Methods," which is hereby incorporated herein by reference in its entirety.

BACKGROUND

Being able to monitor the posture, balance, alertness, and head trauma of a person is of importance to many people for health and social reasons. Accordingly, there is a need for improved systems and methods for monitoring and detecting the physiology of an individual. Various embodiments of the present systems and methods recognize and address the foregoing considerations, and others, of prior art systems and methods.

SUMMARY OF THE VARIOUS EMBODIMENTS

In general, in various embodiments, a computer-implemented method of detecting attributes of a wearer of a computerized wearable device comprising one or more sensors selected from a group consisting of: (1) a gyroscope; (2) an accelerometer; (3) a geomagnetic sensor; (4) a forward facing camera; and (5) an eye-facing camera is used to determine the posture, alertness and whether the wearer has sustained a concussion. The method includes measuring one or more baseline levels from the one or more sensors that are indicative of a normal posture of the wearer. At least partially in response to measuring the baseline levels from the one or more sensors, the method determines a normal posture of the wearer from the measured one or more baseline levels. The method also includes receiving at least one signal from the one or more sensors on the computerized wearable device. At least partially in response to receiving the at least one signal, determining current posture of the wearer of the computerized wearable device. At least partially in response to determining the current posture of the wearer, comparing the current posture of the wearer to the normal posture of the wearer. In addition, the method includes notifying the wearer when the current posture of the wearer deviates from the normal posture of the wearer.

In various other embodiments, the a computerized eyewear comprises (A) at least one processor, (B) one or more sensors operatively coupled to the at least one processor, the one or more sensors selected from a group consisting of: (1) a gyroscope, (2) an accelerometer, (3) a geomagnetic sensor, (4) a pulse oximeter, (5) a forward facing camera, and (6) an eye-facing camera, (C) a power source operatively coupled to the at least one processor, and (D) a communication device operatively coupled to the at least one processor. In particular embodiments, the computerized eyewear is configured to: (1) receive at least one signal from the one or more sensors on the computerized wearable device, (2) at least partially in response to receiving the at least one signal, determine a current physiology of the wearer of the computerized eyewear, (3) at least partially in response to determining the current physiology of the wearer, compare the current physiology of the wearer to a normal physiology of the wearer; and (4) notify the wearer when the current physiology of the wearer deviates from the normal physiology of the wearer.

In yet another embodiment, a computerized wearable device for being worn on a user's head comprises (A) at least one processor, (B) one or more sensors operatively coupled to the at least one processor, the one or more sensors selected from a group consisting of: (1) a gyroscope, (2) an accelerometer, (3) a geomagnetic sensor, (4) a pulse oximeter, (5) a forward facing camera, and (6) an eye-facing camera, (C) a power source operatively coupled to the at least one processor, and (D) a communication device operatively coupled to the at least one processor. In various embodiments, the computerized wearable is configured to: (1) receive at least one signal from the one or more sensors on the computerized wearable device at least partially in response to the wearer experiencing an impact to the wearer's head, (2) at least partially in response to receiving the at least one signal, determine whether the wearer sustained a concussion as a result of experiencing the impact to the wearer's head, and (3) at least partially in response to determining that the wearer sustained a concussion, notify at least one of the wearer or a third party that the wearer has sustained a concussion.

BRIEF DESCRIPTION OF THE DRAWINGS

Various embodiments of systems and methods for detecting attributes a wearer's physiology are described below. In the course of this description, reference will be made to the accompanying drawings, which are not necessarily drawn to scale and wherein.

DETAILED DESCRIPTION OF SOME EMBODIMENTS

Figure 1:
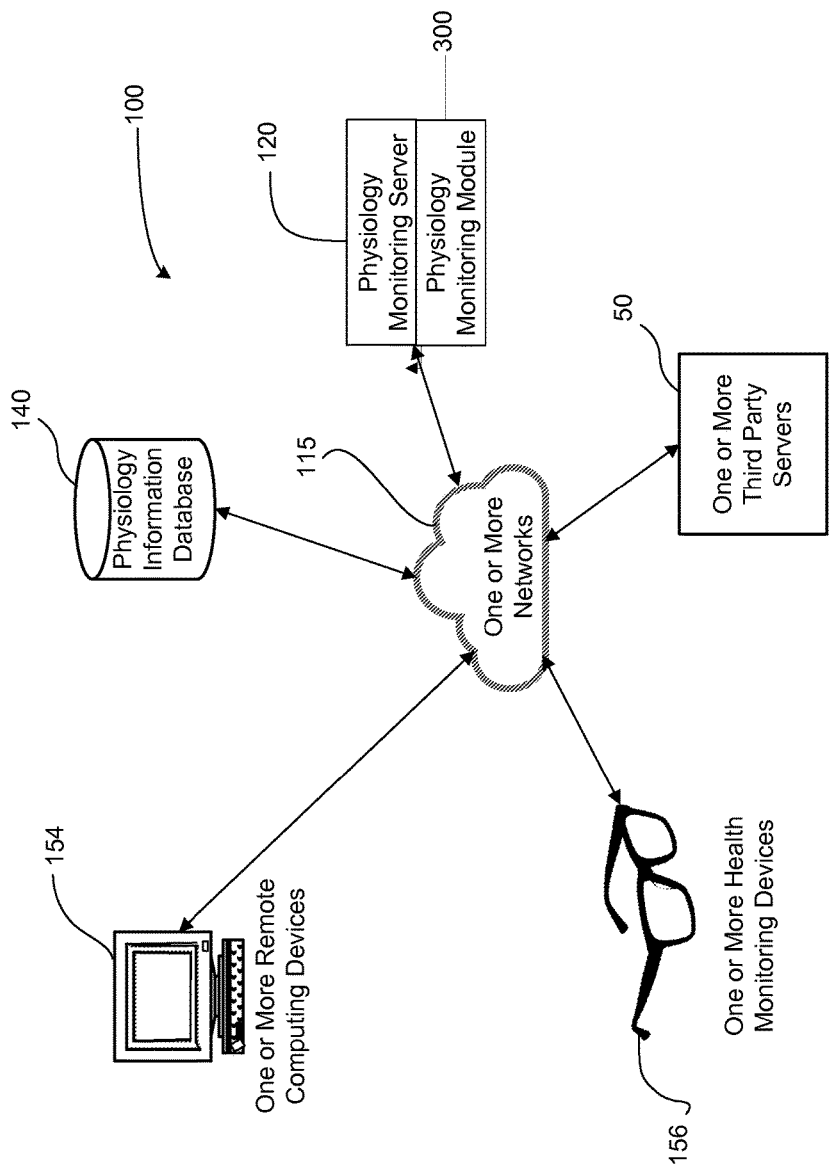
FIG. 1 is a block diagram of a Physiology Monitoring System in accordance with an embodiment of the present system.

Various embodiments will now be described more fully hereinafter with reference to the accompanying drawings. It should be understood that the invention may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Overview

A wearable physiology monitoring system, in various embodiments, may, for example, be embodied in any suitable wearable device configured to monitor the physiology (e.g., posture, balance, alertness, physical injury, etc.) of a wearer. The system may, for example, be embodied as a pair of eyewear, as contact lenses, as a wristwatch, as a suitable piece of clothing (e.g., such as a suitable shirt, pair of pants, undergarment, compression sleeve, etc.), as footwear, as a hat, as a helmet, as an orthopedic cast, or any other suitable wearable item. In a particular example, a wearable physiology monitoring system embodied as a pair of eyewear may enable the system to access one or more (e.g., all five) of a wearer's senses (e.g., touch, sight, sound, smell, and taste) based at least in part on a proximity of the eyewear to the wearer's sensory systems (e.g., eyes, mouth, ears, nose) when worn by the wearer. In other embodiments, a wearable physiology monitoring system embodied as a helmet may enable the system to determine impact, acceleration, posture, and other physiological attributes of the wearer.

In various embodiments, the system comprises one or more sensors configured to determine one or more physiological attributes of the wearer. The one or more sensors may be coupled to the wearable device in any suitable way. For instance, the one or more sensors may be embedded into the wearable device, coupled to the wearable device, and/or operatively coupled to the wearable device. The one or more sensors may include, for example, one or more heart rate monitors, one or more electrocardiogram (EKG) sensors, one or more pedometers, one or more gyroscopes, one or more geomagnetic sensors, one or more thermometers, one or more front-facing cameras, one or more eye-facing cameras, one or more microphones, one or more accelerometers, one or more blood pressure sensors, one or more pulse oximeters, one or more near-field communication sensors, one or more bone scanners, one or more infrared LED/photodiode sensor combinations, one or more photodiode sensors, one or more magnetometers, or any other suitable one or more sensors. In particular embodiments, the system is configured to gather data about the wearer, for example, using the one or more sensors (e.g., such as temperature, balance, heart rate, activity, activity levels, alertness, food eaten, medications taken, steps taken, head position, body movements, facial muscle movements, trauma, etc.).

In some embodiments, one or more body position sensors may be physically or wirelessly coupled to the wearable device and adapted to assess the relative positions of two or more of the wearer's body parts over time in order to determine whether the wearer's posture is desirable or undesirable (e.g., whether the wearer is slouching). For example, the wearable device may include a magnetometer that is adapted to sense the relative positions of a first magnet that a wearer is wearing adjacent the wearer's first shoulder blade (e.g., as an adhesive attachment or embedded within an article of clothing) and a second magnet that the wearer is wearing adjacent the wearer's second shoulder blade (e.g., as an adhesive attachment or embedded within an article of clothing). The system may then use data obtained from the magnetometer regarding the relative positions of the magnets to determine whether the wearer is slouching. In response to determining that the user is slouching, the system may send an alert to the wearer indicating that they should resume a correct posture.

In various embodiments, the sensors determine the physiology of the wearer by monitoring the wearer's orientation, acceleration, geomagnetic field, and images from the one or more front facing cameras and/or one or more eye-facing cameras. The system may measure the wearer's baseline levels based on these characteristics to determine the wearer's normal physiology. The system may measure the wearer's baseline once to create a static baseline, or intermittently to create a dynamic baseline. After determining the wearer's normal physiology based on the baseline levels from the sensors, the system may receive at least one signal from the one or more sensors. The system may use the at least one signal received from the one or more sensors to determine the wearer's current physiology. The system may then compare the wearer's current physiology to the wearer's baseline (e.g., normal) physiology. If the wearer's current physiology deviates from the normal physiology of the wearer, the system may notify the wearer of the deviation. In some embodiments, the system may notify a third party of the deviation. In various embodiments, the system may notify the wearer via the wearable device or through a notification sent to a mobile device associated with the wearer. In some embodiments, the system may also provide suggestions to the wearer on how to change the wearer's current physiology to conform to the wearer's normal physiology. The system, in particular embodiments, may also provide suggestions to the wearer on the cause of the wearer's current physiology. For instance, where the wearer's current physiology (e.g., posture) includes a lowered head and slumped shoulders (as determined by additional sensors placed on the wearer's shoulders) and the wearer's normal physiology (e.g., normal posture) is standing up straight with shoulders back, the system may determine that the wearer is slouching. After determining that the wearer is slouching, the system may notify the wearer to stand up straight or to correct the wearer's current posture to their normal posture. The system may also suggest the cause of the wearer's deviation in posture (e.g., fatigue).

In various embodiments, while the system is using one or more sensors (e.g., eyewear based sensors) to assess the physiology of the wearer, the system may also (e.g., at least substantially simultaneously) capture one or more images of the wearer or the wearer's surroundings (e.g., using a camera, such as a forward-facing camera associated with eyewear worn by the wearer) that may be used in determining the user's activity or physiological state.

Exemplary Technical Platforms

As will be appreciated by one skilled in the relevant field, the present systems and methods may be, for example, embodied as a computer system, a method, or a computer program product. Accordingly, various embodiments may be entirely hardware or a combination of hardware and software. Furthermore, particular embodiments may take the form of a computer program product stored on a computer-readable storage medium having computer-readable instructions (e.g., software) embodied in the storage medium. Various embodiments may also take the form of web-implemented computer software. Any suitable computer-readable storage medium may be utilized including, for example, hard disks, compact disks, DVDs, optical storage devices, and/or magnetic storage devices.

Various embodiments are described below with reference to block diagram and flowchart illustrations of methods, apparatuses, (e.g., systems), and computer program products. It should be understood that each block of the block diagrams and flowchart illustrations, and combinations of blocks in the block diagrams and flowchart illustrations, respectively, can be implemented by a computer executing computer program instructions. These computer program instructions may be loaded onto a general purpose computer, a special purpose computer, or other programmable data processing apparatus that can direct a computer or other programmable data processing apparatus to function in a particular manner such that the instructions stored in the computer-readable memory produce an article of manufacture that is configured for implementing the functions specified in the flowchart block or blocks.

The computer instructions may execute entirely on the user's computer, partly on the user's computer, as a stand-alone software package, partly on a user's computer and partly on a remote computer, or entirely on the remote computer or server. In the latter scenario, the remote computer may be connected to the user's computer through any type of network, including but not limited to: a local area network (LAN); a wide area network (WAN); a cellular network; or the connection may be made to an external computer (for example, through the Internet using an Internet Service Provider).

These computer program instructions may also be stored in a computer-readable memory that can direct a computer or other programmable data processing apparatus to function in a particular manner such that the instructions stored in the computer-readable memory produce an article of manufacture that is configured for implementing the function specified in the flowchart block or blocks. The computer program instructions may also be loaded onto a computer or other programmable data processing apparatus to cause a series of operational steps to be performed on the computer or other programmable apparatus to produce a computer-implemented process (e.g., method) such that the instructions that execute on the computer or other programmable apparatus provide steps for implementing the functions specified in the flowchart block or blocks.

Example System Architecture

FIG. 1 is a block diagram of a Physiology Monitoring System 100 according to particular embodiments. As may be understood from this figure, the Physiology Monitoring System 100 includes One or More Networks 115, One or More Third Party Servers 50, a Physiology Monitoring Server 120 that may, for example, be adapted to execute a Physiology Monitoring Module 300, a Database 140, One or More Remote Computing Devices 154 (e.g., such as a smart phone, a tablet computer, a wearable computing device, a laptop computer, a desktop computer, etc.), and One or More Wearable Health Monitoring Devices 156, which may, for example, be embodied as one or more of eyewear, headwear, clothing, a watch, a hat, a helmet, a cast, an adhesive bandage, a piece of jewelry (e.g., a ring, earring, necklace, bracelet, etc.), or any other suitable wearable device. In particular embodiments, the one or more computer networks 115 facilitate communication between the One or More Third Party Servers 50, the Physiology Monitoring Server 120, Database 140, One or More Remote Computing Devices 154, and the one or more Health Monitoring Devices 156.

The one or more networks 115 may include any of a variety of types of wired or wireless computer networks such as the Internet, a private intranet, a mesh network, a public switch telephone network (PSTN), or any other type of network (e.g., a network that uses Bluetooth or near field communications to facilitate communication between computing devices). The communication link between the One or More Remote Computing Devices 154 and the Mental State Monitoring Server 120 may be, for example, implemented via a Local Area Network (LAN) or via the Internet.

Figure 2:
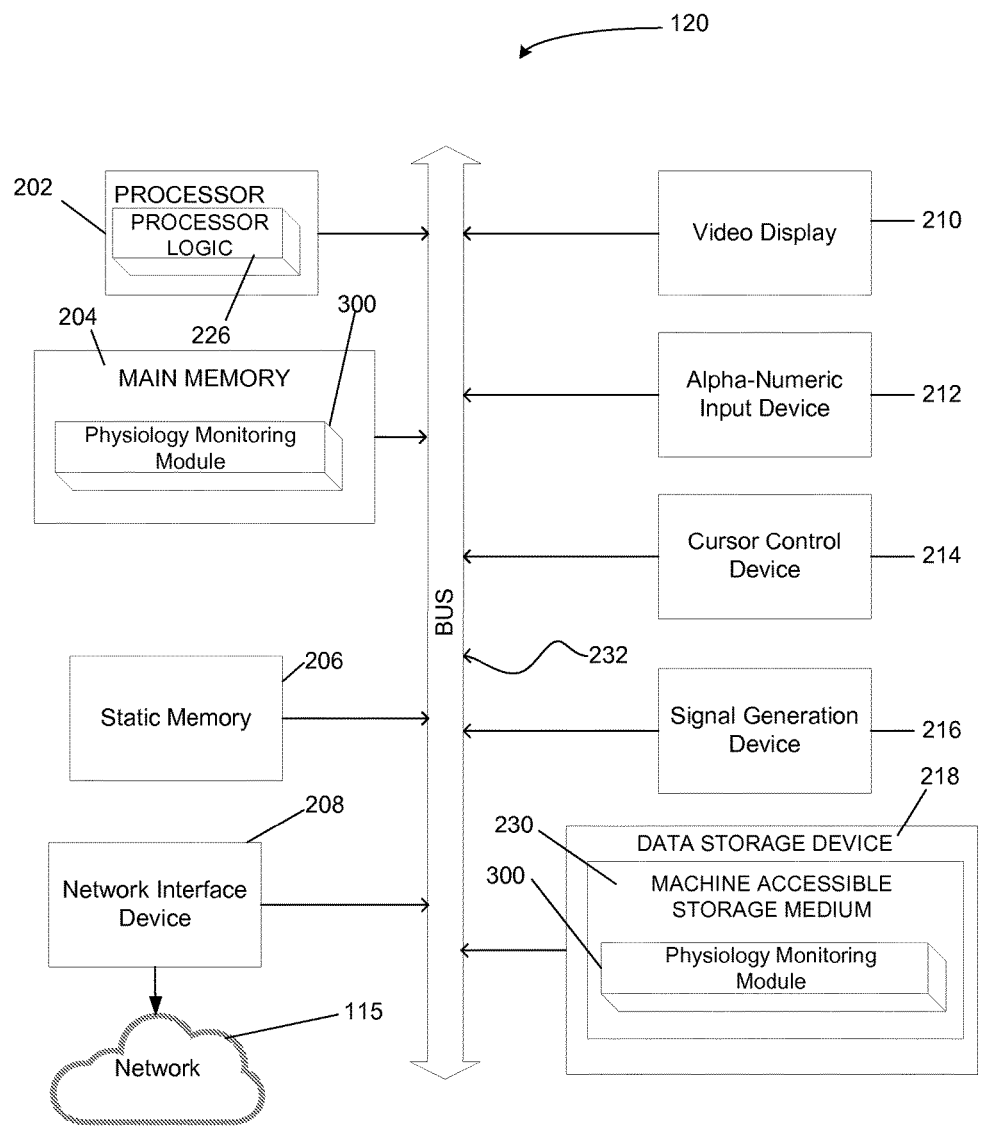
FIG. 2 is a block diagram of the Physiology Monitoring Server of FIG. 1.

FIG. 2 illustrates a diagrammatic representation of the architecture for the Physiology Monitoring Server 120 that may be used within the Physiology Monitoring System 100. It should be understood that the computer architecture shown in FIG. 2 may also represent the computer architecture for any one of the One or More Remote Computing Devices 154, one or more Third Party Servers 50, and one or more Health Monitoring Devices 156 shown in FIG. 1. In particular embodiments, the Physiology Monitoring Server 120 may be suitable for use as a computer within the context of the Physiology Monitoring System 100 that is configured for determining a physiology of a wearer by detecting attributes of the wearer using signals received from sensors coupled to the eyewear.

In particular embodiments, the Physiology Monitoring Server 120 may be connected (e.g., networked) to other computing devices in a LAN, an intranet, an extranet, and/or the Internet as shown in FIG. 1. As noted above, the Physiology Monitoring Server 120 may operate in the capacity of a server or a client computing device in a client-server network environment, or as a peer computing device in a peer-to-peer (or distributed) network environment. The Physiology Monitoring Server 120 may be a desktop personal computing device (PC), a tablet PC, a set-top box (STB), a Personal Digital Assistant (PDA), a cellular telephone, a web appliance, a network router, a switch or bridge, or any other computing device capable of executing a set of instructions (sequential or otherwise) that specify actions to be taken by that computing device. Further, while only a single computing device is illustrated, the term "computing device" shall also be interpreted to include any collection of computing devices that individually or jointly execute a set (or multiple sets) of instructions to perform any one or more of the methodologies discussed herein.

An exemplary Physiology Monitoring Server 120 includes a processing device 202, a main memory 204 (e.g., read-only memory (ROM), flash memory, dynamic random access memory (DRAM) such as synchronous DRAM (SDRAM) or Rambus DRAM (RDRAM), etc.), a static memory 206 (e.g., flash memory, static random access memory (SRAM), etc.), and a data storage device 218, which communicate with each other via a bus 232.

The processing device 202 represents one or more general-purpose or specific processing devices such as a microprocessor, a central processing unit (CPU), or the like. More particularly, the processing device 202 may be a complex instruction set computing (CISC) microprocessor, reduced instruction set computing (RISC) microprocessor, very long instruction word (VLIW) microprocessor, or processor implementing other instruction sets, or processors implementing a combination of instruction sets. The processing device 202 may also be one or more special-purpose processing devices such as an application specific integrated circuit (ASIC), a field programmable gate array (FPGA), a digital signal processor (DSP), network processor, or the like. The processing device 202 may be configured to execute processing logic 226 for performing various operations and steps discussed herein.

The Physiology Monitoring Server 120 may further include a network interface device 208. The Physiology Monitoring Server 120 may also include a video display unit 210 (e.g., a liquid crystal display (LCD) or a cathode ray tube (CRT)), an alpha-numeric input device 212 (e.g., a keyboard), a cursor control device 214 (e.g., a mouse), and a signal generation device 216 (e.g., a speaker).

The data storage device 218 may include a non-transitory computing device-accessible storage medium 230 (also known as a non-transitory computing device-readable storage medium, a non-transitory computing device-readable medium, or a non-transitory computer-readable medium) on which is stored one or more sets of instructions (e.g., the Physiology Monitoring Module 300) embodying any one or more of the methodologies or functions described herein. The one or more sets of instructions may also reside, completely or at least partially, within the main memory 204 and/or within the processing device 202 during execution thereof by the Physiology Monitoring Server 120—the main memory 204 and the processing device 202 also constituting computing device-accessible storage media. The one or more sets of instructions may further be transmitted or received over a network 115 via a network interface device 208.

While the computing device-accessible storage medium 230 is shown in an exemplary embodiment to be a single medium, the term "computing device-accessible storage medium" should be understood to include a single medium or multiple media (e.g., a centralized or distributed database, and/or associated caches and servers) that store the one or more sets of instructions. The term "computing device-accessible storage medium" should also be understood to include any medium that is capable of storing, encoding, or carrying a set of instructions for execution by the computing device and that causes the computing device to include any one or more of the methodologies of the present invention. The term "computing device-accessible storage medium" should accordingly be understood to include, but not be limited to, solid-state memories, optical and magnetic media, etc.

Exemplary System Platform

As noted above, a system, according to various embodiments, is adapted to assess the physiology of a wearer of a wearable device. Various aspects of the system's functionality may be executed by certain system modules, including the Physiology Monitoring Module 300. The Physiology Monitoring Module 300 is discussed in greater detail below.

Physiology Monitoring Module

Figure 3:
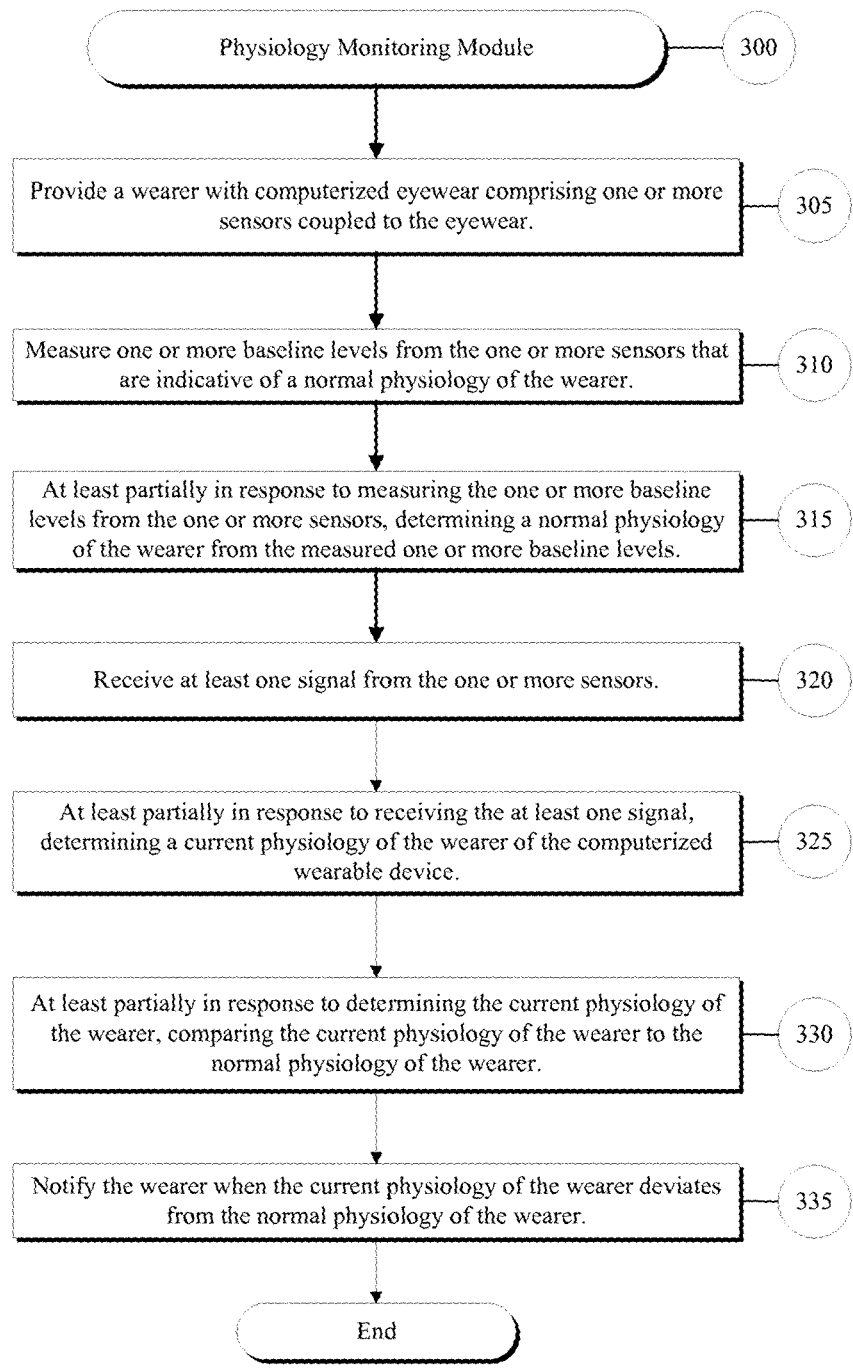
FIG. 3 depicts a flowchart that generally illustrates various steps executed by a Physiology Monitoring Module according to a particular embodiment.

FIG. 3 is a flow chart of operations performed by an exemplary Physiology Monitoring Module 300, which may, for example, run on the Physiology Monitoring Server 120, or any suitable computing device (such as the One or More Health Monitoring Devices 156 or other suitable mobile computing device). In particular embodiments, the Physiology Monitoring Module 300 may assess a wearer's normal physiology and current physiology to determine whether the wearer's current physiology deviates from the wearer's normal physiology.

The system begins, in various embodiments, at Step 305 by providing a wearer with computerized eyewear comprising one or more sensors coupled to the eyewear. In various embodiments, the system may do this by, for example: (1) facilitating delivery of the eyewear to an address associated with a particular individual; (2) facilitating distribution of the eyewear from a healthcare worker to the individual; and (3) placing an order of the eyewear from a third party for delivery to the individual. In other embodiments, this step may be executed manually (e.g., by a human being) rather than a computer.

In various embodiments, the one or more sensors that are coupled to the eyewear (or other health monitoring device, for example, a helmet) are adapted to detect one or more characteristics of a wearer of the eyewear, wherein the one or more characteristics of the wearer are associated with the wearer's physiology. In various embodiments, the sensors coupled to the eyewear or other health monitoring device may include, for example, one or more of the following: a heart rate monitor, an electrocardiogram (EKG), a gyroscope, a geomagnetic sensor, a pedometer, a thermometer, a front-facing camera, an eye-facing camera, a microphone, an accelerometer, a magnetometer, a blood pressure sensor, a pulse oximeter, a skin conductance response sensor, a near-field communication sensor, an infrared LED/photodiode sensor combination, a magnetometer, or any other suitable sensor. In particular embodiments, the sensors coupled to the eyewear comprise one or more of a gyroscope, an accelerometer, a geomagnetic sensor, an impact sensor, an eye-facing camera, and a front-facing camera.

In various embodiments, the one or more sensors are coupled to a computing device that is associated with (e.g., embedded within, attached to) the eyewear or other health monitoring device. In particular embodiments, the eyewear or other health monitoring device comprises at least one processor, computer memory, suitable wireless communications components (e.g., a Bluetooth chip), and a power supply for powering the health monitoring device and/or the various sensors.

Figure 4:
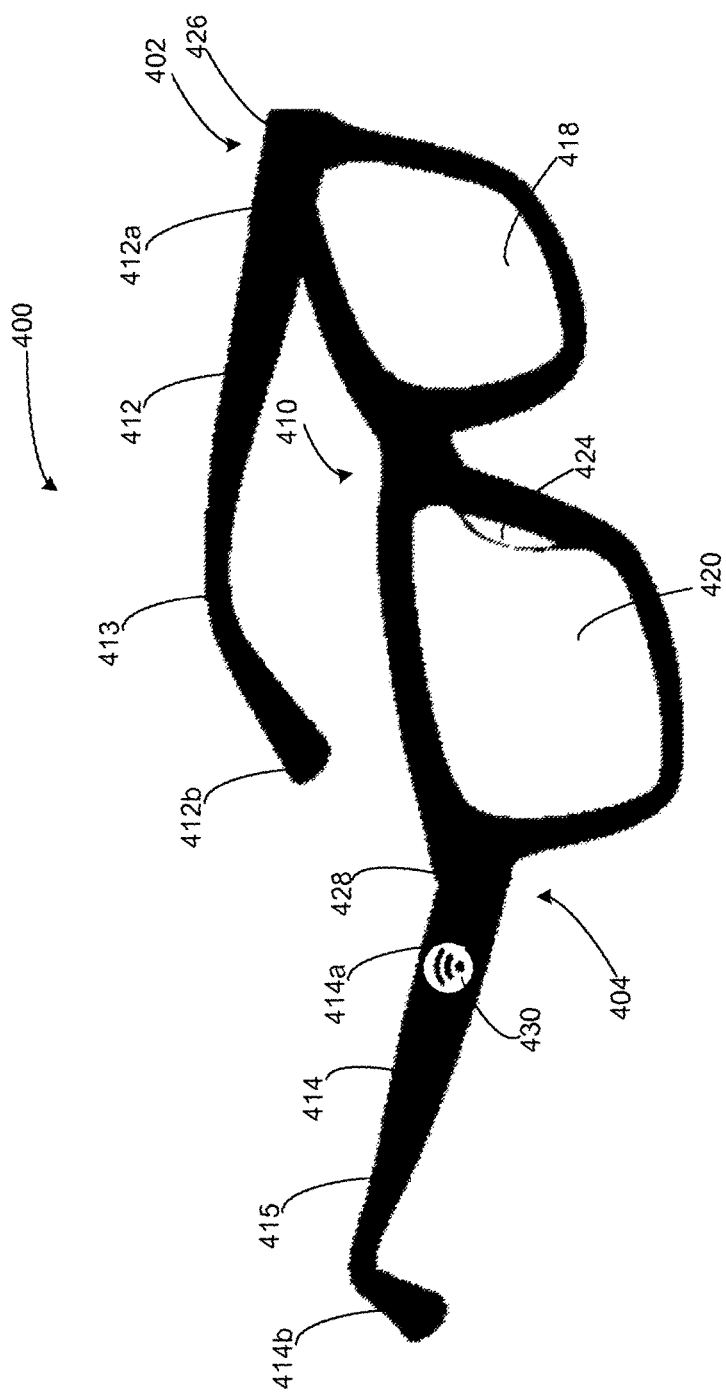
FIG. 4 is an exemplary wearable health monitoring device of FIG. 1.

Referring to FIG. 4, an exemplarily embodiment of eyewear according to particular embodiments illustrates that the one or more sensors may be physically coupled to eyewear 400 in any suitable way. For example, in various embodiments, the one or more sensors may be embedded into the eyewear 400. In some embodiments, the one or more sensors may be positioned along the frame 410 of the eyewear 400. In other embodiments, the one or more sensors may be positioned along the temples 412, 414 of the eyewear 400. In still other embodiments, the one or more sensors may be coupled to one or more of the lenses 418, 420 of the eyewear 400. As noted above, the one or more sensors may be coupled to a Bluetooth device that is configured to transmit the one or more signals to a handheld wireless device, and the step of receiving one or more signals from the one or more sensors (discussed below with reference to Step 320) further comprises receiving the one or more signals from the wireless handheld device (e.g., via the Internet, Wi-Fi, a cellular network, etc.). In particular embodiments, one or more of the one or more sensors may be detachable from the eyewear 400. For instance, if a wearer does not need a temperature sensor or other particular sensor, the sensor may be removed from the eyewear. In other embodiments, the one or more sensors may be detached from the eyewear to attach to other portions of the wearer's body. For example, in determining the posture of the wearer, the gyroscope, accelerometer, or other suitable device may be attached to the wearer's back or shoulders and may be adapted to transmit data to the eyewear. The structure of the eyewear will be discussed further below.

Referring again to FIG. 3, at Step 310, the system measures one or more baseline levels from the one or more sensors that are indicative of a normal physiology of the wearer. In particular embodiments, the one or more baseline levels may be one or more normal starting baseline levels of the wearer. For instance, the pupil size baseline level of the wearer may include that the wearer's eyes are normally dilated because of a medicine the wearer is taking. In other embodiments, the one or more baseline levels may be one or more desired end point baseline levels of the wearer. For instance, where the wearer's normal posture is slouched, the wearer may have the system measure the wearer's posture at the desired end point baseline level of standing up straight. In still other embodiments, the one or more baseline levels may be a baseline level of an average person (e.g., not a baseline level based on measurements from the wearer).

In various embodiments, the system may measure the one or more baseline levels from a single sensor. In other embodiments, the system may measure the one or more baseline levels from all of the sensors. In yet other embodiments, the system may measure the one or more baseline levels from each of the sensors multiple times (e.g., measure baseline levels from the gyroscope three times) to create an average baseline level. In various embodiments, the system may be configured to measure one or more baseline levels from a first sensor at the same time that it measures one or more baseline levels from a second sensor. For example, the system may be configured to receive an orientation from the gyroscope at the same time that it receives a position measurement from the accelerometer. In addition, the system may also receive an oxygen saturation level from a pulse oximeter sensor to determine the wearer's blood oxygen level, which may be used in supplementing position measurements, balance measurements, and alertness measurements.

In various embodiments, the system may measure one or more baseline levels substantially automatically after the sensor generates the data. In particular embodiments, the system may measure one or more baseline levels only once to create a static baseline. For example, the system may measure the wearer's orientation only once to create a static baseline for the wearer's orientation. In some embodiments, the system may measure one or more baseline levels periodically (e.g., by the second, by the minute, hourly, daily, etc.) to create a dynamic baseline. For example, the system may measure the wearer's orientation every thirty seconds throughout the day to create a dynamic baseline for the wearer's orientation. In other embodiments, the system may measure one or more baseline levels after receiving an indication from the wearer and/or a third party that the system should measure the one or more baseline levels. For instance, the wearer may speak a voice command to the wearable device requesting that the device measure the wearer's balance. In various embodiments, the system may receive an indication from the wearer and/or a third party of when to have the system measure the one or more baseline levels. For example, the system may receive an indication from the third party to have the system measure the wearer's orientation at 8:00 a.m. and at 2:00 p.m.

In particular embodiments, the system may measure one or more baseline levels during a predefined time period. In various embodiments, the system may measure one or more baseline levels when a sensor detects movement and/or activities of the wearer (e.g., sitting, lying down, standing, walking, running, lifting, exercising, etc.). For example, the system may measure one or more baseline levels from the gyroscope and/or accelerometer when the sensor detects that the wearer is walking According to some embodiments, the one or more baseline levels may include a normal posture physiology of the average wearer (e.g., not based on measurements from the wearer).

In other embodiments, the one or more baseline levels may include a normal balance physiology of the wearer. For example, the wearer's normal balance may include information on the roll, yaw, and pitch of the wearer's head and/or body while in a particular position (e.g., sitting, lying down, standing, walking, running, lifting, exercising, etc.). In still other embodiments, the one or more baseline levels may include a normal alertness physiology of the wearer. For example, the wearer's normal alertness may include that the wearer is alert, distracted, lethargic, drowsy, sluggish, obtunded, mentally dulled, stuporous, unconscious, unresponsive, etc. The levels of alertness may be determined by data received from one or more sensors (e.g., blink rate, oxygen levels, blood sugar levels, etc.) In yet other embodiments, the one or more baseline levels may include a normal physical state physiology of the wearer. For example, the normal physical state of the wearer may include physical attributes of the wearer (e.g., pupil size, heart rate, perspiration level, respiratory rate, brain wave activity, free of physical injuries, injured, asleep, awake, conscious, unconscious, alive, deceased, stable, good, fair, serious, critical, distressed, etc.).

In particular embodiments, the system may store the one or more baseline levels in associated memory. In various embodiments, the system may store the one or more baseline levels substantially automatically after measuring the data. In other embodiments, the system may store the one or more baseline levels after receiving manual input from the wearer and/or a third party requesting that the system store the baseline levels. In various embodiments, the system may store the one or more baseline levels for a specified period of time. For instance, the system may store the one or more baseline levels for a day, a month, a year, etc., in the Physiology Information Database 140. In some embodiments, the system may store the one or more baseline levels on any suitable server or other device. In other embodiments, the system may store the one or more baseline levels on the Physiology Monitoring Server 120. In still other embodiments, the system may store the one or more baseline levels in an account associated with the wearer. In various embodiments, the system may store the one or more baseline levels with a timestamp of when the one or more baseline levels were received.

At Step 315, at least partially in response to measuring the one or more baseline levels from the one or more sensors, the system determines a normal physiology of the wearer from the measured one or more baseline levels. According to some embodiments, the system may determine the normal physiology of the wearer to be a normal posture of the wearer. For example, the system may determine the wearer's normal posture to be correct. In other embodiments, the system may determine the normal physiology of the wearer to be a normal balance of the wearer. For example, the system may determine that, when standing, the wearer's normal balance is centered over the wearer's right foot, rather than the center of the wearer's stance. In still other embodiments, the system may determine the normal physiology of the wearer to be a normal alertness of the wearer. For instance, the system may determine that the wearer's normal alertness while driving to be alert. In yet other embodiments, the system may determine the normal physiology of the wearer to be a normal physical state of the wearer. For example, the system may determine the wearer's normal physical state to be conscious. In some embodiments, the system may determine the normal physiology of the wearer to be a normal head position of the wearer. For instance, the system may determine that the wearer's normal head position is level. In other embodiments, the system may determine the normal physiology of the wearer to be a normal oxygen level of the wearer. For instance, the system may determine that the wearer's normal oxygen level is 95%. In still other embodiments, the system may determine the normal physiology of the wearer to be a normal pupil size of the wearer. For instance, the system may determine that the wearer's normal pupil size is three millimeters (e.g., 3 mm) in diameter. In various embodiments, the system may determine the normal physiology of the wearer to be a normal pitch, roll, and yaw of the wearer's head. For instance, the system may determine that the wearer's normal head pitch is even about the right-left axis, the wearer's normal head roll is even about the inferior-superior axis, and the wearer's normal head yaw is even about the anterior-posterior axis.

In particular embodiments, the system determines a normal physiology of the wearer by averaging the one or more baseline levels. For instance, the system may determine the wearer's normal posture by averaging the wearer's baseline levels for posture. In yet other embodiments, the system may determine the wearer's normal posture based on a baseline posture of the average wearer.

In various embodiments, the system determines a normal physiology of the wearer substantially automatically after measuring the one or more baseline levels. In some embodiments, the system may determine the wearer's normal physiology periodically (e.g., by the second, by the minute, hourly, daily, etc.). For example, the system may determine the wearer's normal physiology every thirty seconds throughout the day. In other embodiments, the system may determine the wearer's normal physiology after receiving an indication from the wearer and/or a third party that the system should determine the wearer's normal physiology. For instance, the wearer may speak a voice command to the wearable device requesting that the device determine the wearer's normal posture. In various embodiments, the system may receive an indication from the wearer and/or a third party of when to have the system determine the wearer's normal physiology. For example, the system may receive an indication from the third party to have the system determine the wearer's normal balance at 8:00 a.m. and at 2:00 p.m.

In particular embodiments, the system may store the normal physiology of the wearer in an account associated with the wearer. In some embodiments, the normal physiology of the wearer may be accessible by the wearer and/or a third party. For instance, the normal physiology of the wearer may be diagramed in a chart that is accessible from the wearable device or from a computing device by the wearer and/or the wearer's physician. In various embodiments, the system may store the normal physiology of the wearer in the Physiology Information Database 140. In particular embodiments, the system may store information in the Physiology Information Database 140 regarding past normal physiologies of the wearer associated with the wearer (e.g., the wearer used to slouch, but no longer slouches, etc.).

At Step 320, the system receives at least one signal from the one or more sensors. In particular embodiments, the at least one signal may include one or more signals that may be used to derive: (1) the wearer's a heart rate, (2) the wearer's heart rhythm; (3) a distance traveled by the wearer; (4) the wearer's body temperature; (5) one or more images associated with the wearer or the wearer's environment; (6) one or more sounds associated with the wearer's body or the wearer's environment; (7) a speed traveled by the wearer; (8) the wearer's blood pressure; (9) the wearer's oxygen saturation level; (10) the wearer's brainwave activity; (11) the wearer's pupil size; (12) the wearer's perspiration level; (13) the wearer's respiratory rate; (14) the number and/or cadence of steps taken by the wearer; (15) the movement of one or more of the wearer's facial muscles; (16) one or more biochemical changes within the wearer's body (e.g., changes in hormone levels, releases of neurotransmitters); (17) changes in the one or more characteristics of the wearer's skin (e.g., skin paleness or clamminess); (18) one or more postures associated with the wearer; and/or (19) any other suitable attribute of the wearer or the wearer's environment. For instance, the system may receive a signal from an eye-facing camera associated with the eyewear that the wearer is looking down at the same time that the system receives a signal from the front-facing camera that there is a road in front of the wearer. In various embodiments, the system may store data related to the signals and/or data derived from this data for later review and use in determining the physiology of the wearer.

In particular embodiments, the system may receive one or more of the above-referenced signals substantially automatically. In various embodiments, the system may receive one or more of the signals on a substantially periodic basis (e.g., by the second, by the minute, hourly, daily, etc.). For example, the system may receive one or more signals every thirty seconds throughout the day. In other embodiments, the system may receive one or more signals at least partially in response to receiving an indication from the wearer that the system should receive a signal. For instance, the wearer may speak a voice command to the wearable device requesting that the device receive a signal from the gyroscope to get the wearer's orientation. In various embodiments, the system may receive an indication from the wearer of when to have the system receive the signal. For example, the system may receive an indication from the wearer to have the system receive a signal from the gyroscope at 8:00 a.m. and at 2:00 p.m. on a particular day. In particular embodiments, the system may receive a request from the wearer to have a particular signal received from a particular sensor at the same time that the system receives a second particular signal from a second particular sensor. For example, when the system receives a signal that indicates that the wearer's pupil size has increased, the system may, at least partially in response to receiving the increased pupil size signal, also obtain an orientation of the wearer from the gyroscope associated with the eyewear. In various embodiments, the system may receive at least one signal from one of an accelerometer and a gyroscope. In some of these embodiments, the system may receive at least one signal from the one or more sensors at least partially in response to the wearer experiencing an impact to the wearer's head. The system may also determine an intensity level of the impact experienced by the wearer based on the at least one signal or based on at least another signal.

In some embodiments, the system receives a signal of an image captured by the eyewear. In various embodiments, the system receives a plurality of images captured by the eyewear. In particular embodiments, the system receives the image from the front-facing camera. In some embodiments, the system receives the image substantially automatically from the front-facing camera. In other embodiments, the system may receive the image in response to receiving an indication from the wearer to capture the image. For example, the system may receive a voice command from the wearer to capture the image. In various embodiments, the system may store the captured image in local or remote memory. In some embodiments, the image captured by the eyewear may be a video.

In various embodiments, the system may receive only one signal from a single sensor associated with the eyewear. In other embodiments, the system may receive a signal from a plurality of the sensors associated with the eyewear. In yet other embodiments, the system may receive multiple signals from one or more of the sensors. In various embodiments, the system may be configured to receive a first signal from a first sensor at the same time that it receives a second signal from a second sensor. For example, the system may be configured to receive an image signal from an eye-facing camera associated with the eyewear at the same time that the system receives an orientation signal from the gyroscope associated with the eyewear. As a further example, the system may be configured to simultaneously receive a signal from both an eye-facing camera and a brainwave activity sensor associated with the eyewear.

At Step 325, at least partially in response to receiving the at least one signal, the system determines a current physiology of the wearer. According to some embodiments, the system may determine the current physiology of the wearer to be a current posture of the wearer. For instance, the system may determine the wearer's current posture to be slouched posture. In other embodiments, the system may determine the current physiology of the wearer to be a current balance of the wearer (e.g., while sitting, standing, laying down, etc.). For instance, the system may determine the wearer's current balance, while standing, to be centered over the center of the wearer's stance. In still other embodiments, the system may determine the current physiology of the wearer to be a current alertness of the wearer. For instance, the system may determine the wearer's current alertness while driving to be distracted. In yet other embodiments, the system may determine the current physiology of the wearer to be a current physical state of the wearer. For instance, the system may determine the wearer's current physical state is unconscious.

In still other embodiments, the system may determine the current physiology of the wearer to be a current head position of the wearer. For instance, the system may determine the wearer's current head position to be lowered. In other embodiments, the system may determine the current physiology of the wearer to be a current pitch, roll, and yaw of the wearer's head. For example, the system may determine the wearer's current head pitch is 45 degrees to the right about the right-left axis, the wearer's current head roll is even about the inferior-superior axis, and the wearer's current head yaw is even about the anterior-posterior axis.

In various embodiments, the system may determine the current physiology of the wearer to be a current oxygen level of the wearer. For example, the system may determine the wearer's current oxygen level is 90%. In particular embodiments, the system may, at least partially in response to determining that the wearer is sitting, determine based on the oxygen level of the wearer an alertness level of the wearer. In some embodiments, in determining the current posture of the wearer, the system may also detect that the wearer's head is tilted downward. In yet other embodiments, in response to determining an oxygen level for the wearer, the system determines an alertness of the wearer at least partially based on the current posture and the oxygen level of the wearer. In still other embodiments, the system may determine an alertness level of the wearer at least partially based on the current pitch, roll, and yaw of the wearer's head and the current oxygen level of the wearer.

In particular embodiments, the system may determine the current physiology of the wearer to be a current pupil size of the wearer. For example, the system may determine the wearer's current pupil size is seven millimeters (e.g., 7 mm). In various embodiments, the system may determine the current physiology of the wearer in response to the wearer experiencing an impact to the wearer's head to determine whether the wearer sustained a concussion as a result of experiencing the impact to the wearer's head.

In various embodiments, the system determines a current physiology of the wearer substantially automatically after receiving the at least one signal from the one or more sensors. In some embodiments, the system may determine the wearer's current physiology periodically (e.g., by the second, by the minute, hourly, daily, etc.). For example, the system may determine the wearer's current physiology every thirty seconds throughout the day. In other embodiments, the system may determine the wearer's current physiology after receiving an indication from the wearer and/or a third party that the system should determine the wearer's current physiology. In various embodiments, the system may receive an indication from the wearer and/or a third party of when to have the system determine the wearer's current physiology. For example, the system may receive an indication from the third party to have the system determine the wearer's current balance at 8:00 a.m. and at 2:00 p.m.

In particular embodiments, the system may store the current physiology of the wearer in an account associated with the wearer. In some embodiments, the current physiology of the wearer may be accessible by the wearer and/or a third party. For instance, the current physiology of the wearer may be diagramed in a chart that is accessible from the wearable device or from a computing device by the wearer's physician. In various embodiments, the system may store the current physiology of the wearer in the Physiology Information Database 140.

At Step 330, at least partially in response to determining the current physiology of the wearer, the system compares the current physiology of the wearer to the normal physiology of the wearer. According to some embodiments, the system may compare the current posture of the wearer to the normal posture of the wearer. In particular embodiments, the system may compare the current alertness of the wearer to the normal alertness of the wearer. In some embodiments, the system may compare the current head position of the wearer to the normal head position of the wearer. In particular embodiments, the system may compare the current oxygen level of the wearer to the normal oxygen level of the wearer. In other embodiments, the system may compare the current pupil size of the wearer to the normal pupil size of the wearer. In still other embodiments, the system may compare the current pitch, roll, and/or yaw of the wearer's head to the normal pitch, roll, and/or yaw of the wearer's head. In various embodiments, the system may compare one or more of the current head position (e.g., pitch, roll, and yaw, etc.), current oxygen level, current pupil size, etc. to the normal measurements to determine one or more or the wearer's posture, alertness or level of consciousness.

In some embodiments, the system compares the wearer's current physiology to the wearer's normal physiology substantially automatically after the system determines the current physiology of the wearer. In various embodiments, the system compares the wearer's current physiology to the wearer's normal physiology after detecting a particular event. For instance, if the system detects an impact, the system may compare the wearer's current physical state to the wearer's normal physical state to determine whether the wearer is conscious. In some embodiments, the system may compare the wearer's current physiology to the wearer's normal physiology periodically (e.g., by the second, by the minute, hourly, daily, weekly, monthly, etc.). For example, the system may compare the wearer's current posture to the wearer's normal posture every thirty minutes throughout the day. In other embodiments, the system may compare the wearer's current physiology to the wearer's normal physiology after receiving an indication from the wearer or a third party that the system should compare the wearer's current physiology to the wearer's normal physiology. For instance, the wearer may speak a voice command to the wearable device requesting that the device compare the wearer's current alertness to a normal alertness established the previous month. In various embodiments, the system may receive an indication from the wearer and/or a third party of when to have the system compare the wearer's current physiology to the wearer's normal physiology. For example, the system may receive an indication from the wearer to have the system compare the wearer's posture to the normal posture of the wearer at 8:00 a.m. and at 2:00 p.m. on a particular day.

In various embodiments, the system may compare the wearer's current physiology to the wearer's normal physiology to determine if the wearer's current physiology deviates from the wearer's normal physiology. In particular embodiments, the wearer's current physiology may not deviate from the wearer's normal physiology. In other embodiments, the wearer's current physiology may deviate from the wearer's normal physiology. In particular embodiments, the system may detect one or more deviations from the wearer's normal physiology. In various embodiments, the system may determine the wearer's current physiology deviates from the wearer's normal physiology based on a predetermined percentage. For instance, the system may determine a wearer's current pupil size deviates from the wearer's normal pupil size if the wearer's current pupil size is 10% larger than the wearer's normal pupil size.

In some embodiments, the wearer's current posture may deviate from the wearer's normal posture. For instance, where the wearer's normal posture is correct, the system may determine that the wearer's current posture of slouched deviates from the wearer's normal posture. In other embodiments, the wearer's current balance may deviate from the wearer's normal balance. For example, where the wearer's normal balance while standing is centered over the wearer's right foot rather than the center of the wearer's stance, the system may determine the wearer's current balance of centered over the center of the wearer's stance while standing deviates from the wearer's normal balance. In still other embodiments, the wearer's current alertness may deviate from the wearer's normal alertness. For instance, where the wearer's normal alertness while driving is alert, the system may determine the wearer's current alertness of distracted while driving deviates from the wearer's normal alertness. In yet other embodiments, the wearer's physical state may deviate from the wearer's normal physical state. For example, where the wearer's normal physical state is conscious, the system may determine the wearer's current physical state of unconscious deviates from the wearer's normal physical state.

In some embodiments, the wearer's current head position may deviate from the wearer's normal head position. For instance, where the wearer's normal head position is level, the system may determine the wearer's current head position of lowered deviates from the wearer's normal head position, when standing or driving. In other embodiments, the wearer's current oxygen level may deviate from the wearer's normal oxygen level. For example, where the wearer's normal oxygen level is 95%, the system may determine the wearer's current oxygen level of 90% deviates from the wearer's normal oxygen level. In particular embodiments, the wearer's current pupil size may deviate from the wearer's normal pupil size. For instance, where the wearer's normal pupil size is three millimeters, the system may determine the wearer's current pupil size of seven millimeters deviates from the wearer's normal pupil size. In various embodiments, the system may determine if the wearer's current pupil size exceeds a predetermined pupil size. For example, the system may determine that the wearer's current pupil size of eight millimeters exceeds the predetermined pupil size of three millimeters.

In some other embodiments, the pitch, roll, and/or yaw of the wearer's head may deviate from the normal pitch, roll, and/or yaw of the wearer's head by a predetermined amount. For instance, where the wearer's normal head pitch is even about the right-left axis, the system may determine the wearer's current head pitch of 45 degrees to the right about the left-right axis deviates from the wearer's normal head pitch. In other embodiments, the intensity level of an impact experienced by the wearer may exceed a predetermined intensity level. For example, where the predetermined intensity level is a particular intensity level, the system may determine the current intensity level of the impact experienced by the wearer exceeds the predetermined intensity level by 20%.

In particular embodiments, the system may store the comparisons in an account associated with the wearer. In some embodiments, the comparisons may be accessible by the wearer and/or a third party. For instance, the comparisons may be diagramed in a chart that is accessible from the wearable device or from a computing device by the wearer's physician.

At Step 335, the system notifies the wearer when the current physiology of the wearer deviates from the normal physiology of the wearer. In particular embodiments, the system may notify a third party when the wearer's current physiology deviates from the wearer's normal physiology. In some embodiments, in addition to notifying the wearer, the system may update the wearer's account to note that a notification was sent. In particular embodiments, the system may notify the wearer of the deviation from the normal physiology by displaying an image on the lens of the eyewear. In other embodiments, the system notifies the wearer of the deviation from the normal physiology by communicating through a speaker to the wearer. In various embodiments, the system may notify the wearer of the deviation from the normal physiology by sending an electric shock to the wearer.

In some embodiments, the system notifies the wearer and/or the third party of the deviation from the normal physiology by sending a notification to the wearer's and/or the third party's mobile device. In particular embodiments, the system notifies the wearer and/or the third party of the deviation from the normal physiology by email and/or text message. In other embodiments, the system may notify the wearer and/or the third party of a single deviation from the normal physiology substantially immediately after the system detects the deviation between the wearer's current physiology as compared to the wearer's normal physiology. In yet other embodiments, the system may notify the wearer and/or the third party of all deviations detected on a particular day at the end of that day.

In various embodiments, the system may notify the wearer and/or the third party of the deviation from the normal physiology after a particular event. For example, the system may notify a third party of the wearer's current physical state of unconscious if the system determines that the wearer has experienced an impact. In some embodiments, the system may notify the wearer and/or the third party of the deviation from the normal physiology after a particular period of time. For instance, the system may notify the wearer of the deviation from the wearer's normal correct posture to a current posture of slouched after one hour of detecting the wearer in the slouched posture. In still other embodiments, the system may notify the wearer of the one or more deviations from the wearer's normal physiology at a particular time of day. As an example, the system may notify the wearer of the deviation from the wearer's normal posture to the wearer's current posture at the end of the day.

In particular embodiments, the system may notify the wearer of the deviation from the wearer's normal posture physiology (e.g., head position) to the wearer's current posture physiology. In some embodiments, the system may notify the wearer of the deviation from the wearer's normal balance physiology to the wearer's current balance physiology. In other embodiments, the system may notify the wearer of the deviation from the wearer's normal alertness physiology to the wearer's current alertness physiology. In still other embodiments, the system may notify the wearer of the deviation from the wearer's normal physical state physiology to the wearer's current physical state physiology. In some embodiments, the system may notify the wearer of the deviation from the wearer's normal oxygen level physiology to the wearer's current oxygen level physiology. In other embodiments, the system may notify the wearer of the deviation from the wearer's normal pupil size physiology to the wearer's current pupil size physiology. In still other embodiments, the system may notify the wearer of the deviation from the wearer's normal head pitch, roll, and yaw physiology to the wearer's current head pitch, roll, and yaw physiology.

In various embodiments, at least partially in response to determining that the wearer sustained a concussion, the system may notify one of the wearer or a third party that the wearer has sustained a concussion. In particular embodiments, at least partially in response to the intensity level of the impact experienced by the wearer exceeding the predetermined intensity level, the system may notify one of the wearer or a third party that the wearer has sustained a concussion. In some embodiments, at least partially in response to the measured pupil size exceeding a predetermined pupil size, the system may confirm that the wearer has sustained a concussion.

In various embodiments, in addition to notifying the wearer of the deviation from the normal physiology, the system may also provide suggestions to the wearer on how to change the wearer's current physiology to make it conform to the wearer's normal physiology. For instance, where the wearer's normal physiology is correct posture and the wearer is currently slouching, the system may suggest for the wearer to stand up straight. Alternatively, if the wearer is sitting down in a car and slouching, the system may suggest that the wearer press the back of their head into the headrest, which will cause the user to tighten their neck muscles also causing their shoulders to pull back out of the slouching position. In some embodiments, the system may also provide suggestions to the wearer on the cause of the wearer's current physiology. For example, where the wearer's normal physiology is correct posture and the wearer is currently slouching, the system may provide a suggestion to the wearer that the cause of the wearer's current physiology may be fatigue or a more serious medical issue such as depression based on the user's posture and other physiological attributes measured by the one or more sensors.

In various embodiments, the system, when executing the Physiology Monitoring Module 300, may omit particular steps, perform particular steps in an order other than the order presented above, or perform additional steps not discussed directly above.

Structure of the Eyewear

Referring again to FIG. 4, eyewear 400, according to various embodiments, includes: (1) the eyewear frame 410; (2) the first temple 412; and (3) the second temple 414. These various components are discussed in more detail below.

Eyewear Frame

Referring still to FIG. 4, eyewear 400, in various embodiments, includes any suitable eyewear frame 410 configured to support one or more lenses 418, 420. In the embodiment shown in this figure, the eyewear frame 410 has a first end 402 and a second end 404. The eyewear frame 410 may be made of any suitable material such as metal, ceramic, polymers or any combination thereof. In particular embodiments, the eyewear frame 410 is configured to support the first and second lenses 418, 420 about the full perimeter of the lenses. In other embodiments, the eyewear frame 410 may be configured to support the first and second lenses 418, 420 about only a portion of each respective lens. In various embodiments, the eyewear frame 410 is configured to support a number of lenses other than two lenses (e.g., a single lens, a plurality of lenses, etc.). In particular embodiments, the lenses 418, 420 may include prescription lenses, sunglass lenses, or any other suitable type of lens (e.g., reading lenses, non-prescription lenses), which may be formed from glass or polymers.

The eyewear frame 410 includes a first (not shown in figure) and second nose pad 424, which may be configured to maintain the eyewear 400 adjacent the front of a wearer's face such that the lenses 418, 420 are positioned substantially in front of the wearer's eyes while the wearer is wearing the eyewear 400. In particular embodiments, the nose pads may comprise a material that is configured to be comfortable when worn by the wearer (e.g., rubber, polymer, etc.). In other embodiments, the nose pads may include any other suitable material (e.g., plastic, metal, etc.). In still other embodiments, the nose pads may be integrally formed with the frame 410 and made from the same material as the frame.

The eyewear frame 410 includes a first and a second hinge 426, 428, that attach the first and second temples 412, 414 to the frame first and second ends 402, 404, respectively. In various embodiments, the hinges may be formed by any suitable connection (e.g., tongue and groove, ball and socket, spring hinge, etc.). In particular embodiments, the first hinge 426 may be welded to, or integrally formed with, the frame 410 and the first temple 412 and the second hinge 428 may be welded to, or integrally formed with, the frame 410 and the second temple 414.

First and Second Temples

As shown in FIG. 4, the first temple 412, according to various embodiments, is rotatably connected to the frame 410 at a right angle to extend the first temple 412 substantially perpendicular, substantially parallel, or anywhere in between the right angle to the frame 410. The first temple 412 has a first and second end 412a, 412b. Proximate the first temple second end 412b, the first temple 412 includes an earpiece 413 configured to be supported by a wearer's ear. Similarly, the second temple 414, according to various embodiments, is rotatably connected to the frame 410 at a right angle to extend the second temple 414 substantially perpendicular, substantially parallel, or anywhere in between the right angle to the frame 410. The second temple 414 has a first and second end 414a, 414b. Proximate the second temple second end 414b, the second temple 414 includes an earpiece 415 configured to be supported by a wearer's ear.

Sensors

In various embodiments, the second temple 414 has one or more sensors 430 connected to the second temple 414. As discussed above, in various embodiments, the one or more sensors 430 may be coupled to the frame 410, the first and second temples 412, 414, the first and second lenses 418, 410, or any other portion (e.g., the nose pads, etc.) of the eyewear 400 in any suitable way. For instance, the one or more sensors 430 may be embedded into the eyewear 400, coupled to the eyewear 400, and/or operatively coupled to the eyewear 400. In various embodiments, the one or more sensors 430 may be formed at any point along the eyewear 400. For instance, a fingerprint reader may be disposed adjacent the first temple of the eyewear 400. In various embodiments, the one or more sensors 430 may be formed in any shape. In addition, the one or more sensors 430 may be formed on the inner (back) surface of the frame 410, the first and second temples 412, 414, the first and second lenses 418, 410, or any other portion of the eyewear 400. In other embodiments, the one or more sensors 430 may be formed on the outer (front) surface of the frame 410, the first and second temples 412, 414, the first and second lenses 418, 410, or any other portion of the eyewear 400.

In various embodiments, the one or more sensors 430 that are coupled to the eyewear (or other wearable device) are adapted to detect one or more characteristics of the eyewear or a wearer of the eyewear, wherein the one or more characteristics of the eyewear or the wearer are associated with the wearer's physiology. In various embodiments, the one or more sensors coupled to the eyewear or other wearable device may include, for example, one or more of the following: a near-field communication sensor, a Bluetooth chip, a GPS unit, an RFID tag (passive or active), a fingerprint reader, an iris reader, a retinal scanner, a voice recognition sensor, a heart rate monitor, an electrocardiogram (EKG), an electroencephalogram (EEG), a pedometer, a thermometer, a front-facing camera, an eye-facing camera, a microphone, an accelerometer, a magnetometer, a blood pressure sensor, a pulse oximeter, a skin conductance response sensor, any suitable biometric reader, an infrared LED sensor, a photodiode sensor, a magnetometer, or any other suitable sensor. In some embodiments, the one or more sensors may include a unique shape, a unique code, or a unique design physically inscribed into the eyewear that may be readable by an individual or a remote computing device.

In various embodiments, the one or more sensors are coupled to a computing device that is associated with (e.g., embedded within, attached to) the eyewear or other wearable device. In particular embodiments, the eyewear or other wearable device comprises at least one processor, computer memory, suitable wireless communications components (e.g., a Bluetooth chip) and a power supply for powering the wearable device and/or the various sensors.

As noted above, the one or more sensors may be coupled to a Bluetooth device that is configured to transmit the one or more signals to a handheld wireless device, and the step of using the eyewear to measure the one or more baseline levels from the one or more sensors (discussed above in reference to Step 310) further comprises receiving the one or more signals from the wireless handheld device (e.g., via the Internet). In particular embodiments, one or more of the sensors may be detachable from the eyewear. For instance, if a wearer does not need a temperature sensor or other particular sensor, the sensor may be removed from the eyewear.

Exemplary User Experience

Monitor Driver Alertness

In a particular example of a wearer using the Physiology Monitoring Module 300 to monitor their physiology, the wearer may put on the wearable device (e.g., computerized eyewear) as the wearer enters a vehicle to begin driving. During this time, the system tracks the alertness of the wearer using the system's orientation sensor(s), brainwave activity sensor, blink rate sensor, oxygen sensor, infrared LED, photodiode sensor, front-facing camera, and/or eye-facing camera. The wearer may begin by having the system take a baseline measurement of the wearer's alertness while the wearer is looking straight ahead out of the windshield of the vehicle. In this baseline alertness physiology of the wearer, the wearer's head is raised, eyes are focused on the road ahead, the wearer's blink rate is normal, the wearer is sitting up straight, and the wearer is alert and conscious. The system then tracks the current physiology of the wearer including the wearer's posture, balance, alertness, and physical state. For instance, if the wearer looks down, the system will track the wearer's head movements and may also capture an image of what the wearer is looking at. In this case, the wearer may be looking down at a mobile device for longer than a predetermined time period and the system may determine that the wearer's current physiology deviates from the wearer's normal physiology. Based on the determination of the deviation from the normal physiology, the system may flash a message on the wearable device's lens to notify the wearer that the wearer should be looking at the road rather than at the wearer's mobile device. In another example, the wearer's blink rate and/or blink frequency may increase or decrease. For instance, where the wearer has become tired, the wearer's frequency of blinks may decrease as the wearer's eyes remain closed for longer periods of time. The system may then determine that the wearer's current alertness deviates from the wearer's normal alertness. In response to determining a particular deviation from the wearer's normal alertness level (e.g., as determined by changes in the wearer's blink rate), the system may emit a sound, or other alert, to notify the wearer (or other individual) that the wearer's alertness level is too low to be driving.

Assist with Posture Correction

Similar to the system tracking driver alertness, the system, in a particular example, will also allow a wearer to correct his or her posture. For example, where a wearer has poor normal posture as designated by slumped shoulders, the wearer may begin using the wearable device by creating a baseline level of posture at a correct posture of standing up straight, which includes an inward curve at the neck, an outward curve at the upper back, and an inward curve at the lower back. After putting on the wearable device, which includes additional sensors for the wearer's back, the wearer assumes the correct posture and can speak a command to the wearable device to measure the wearer's normal posture at the correct posture position. The wearer may then continue to wear the wearable device with the additional sensors while striving to achieve the correct posture. If the system determines that the wearer has deviated from the correct posture, the system may send an alert to the wearer requesting the wearer to return to the wearer's normal posture and assume the correct posture by standing up straight. In this scenario, the wearer may have the notification set to notify the wearer substantially automatically once a deviation occurs so that the wearer may actively correct his or her posture throughout the day. In various embodiments, the system may be configured to provide the wearer with suggestion on how the wearer can correct their current posture to the normal correct posture. Moreover, in some embodiments, the system can take continuing measurements to ensure that the wearer has reached a current position that substantially places the wearer's posture into a correct position.

Identify a Concussion

In a further particular example of a wearer using the Physiology Monitoring Module 300 of the One or More Wearable Health Monitoring Devices 156 to monitor the wearer's physiology, the wearable monitoring device may be embedded in an athletic helmet such as a football helmet. Prior to a game or a practice, the wearer may put the athletic helmet on and create a baseline level to include the wearer's posture, balance, alertness, and physical state. During the game or the practice, if the system determines that any of the wearer's current physiologies deviate from the wearer's normal physiology, the system may alert the wearer's coach and/or parent(s). For example, if after experiencing a sudden impact, the system determines that the wearer's pupils have become dilated and/or the wearer loses consciousness, the system will notify the wearer's coach that the wearer may have sustained a concussion.

Identify Diseases

In another example, the Physiology Monitoring Module 300 may be used to determine one or more diseases in one or more persons. For instance, an elementary school may purchase a single wearable device with the Physiology Monitoring Module 300 to detect scoliosis in school-age children. The school may create the baseline level of correct spinal posture by manually entering the normal posture into the system. The school may then place the wearable device with the additional sensors for the wearer's shoulders and back on each child (e.g., for a predetermined period of time, etc.) to determine if the child's posture deviates from the normal posture entered into the system. If a particular child's posture deviates, the system may notify the school that the deviation may be indicative of the particular child having scoliosis.

CONCLUSION

Many modifications and other embodiments of the invention will come to mind to one skilled in the art to which this invention pertains, having the benefit of the teaching presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for the purposes of limitation.

What is claimed is:

1. A computerized eyewear comprising:
   a. at least one processor;
   b. one or more sensors operatively coupled to the at least one processor, the one or more sensors selected from the group consisting of:
      i. a gyroscope,
      ii. an accelerometer,
      iii. a geomagnetic sensor,
      iv. a pulse oximeter,
      v. a forward facing camera, and
      vi. an eye-facing camera;
   c. a power source operatively coupled to the at least one processor; and
   d. a communication device operatively coupled to the at least one processor;
   wherein the computerized eyewear is configured to:
      i. receive at least one signal at first time or a first period of time from the one or more sensors;
      ii. receive at least one signal at a second time or a second period of time from the one or more sensors;
      iii. at least partially in response to receiving the at least one signal at the first time or the first period of time, determine a baseline physiology of the wearer of the computerized eyewear;
      iv. utilize the baseline physiology to determine a normal physiology of the wearer;
      v. at least partially in response to receiving the at least one signal at the second time or the second period of time, determine a current physiology of the wearer of the computerized eyewear;
      vi. at least partially in response to determining the current physiology of the wearer, compare the current physiology of the wearer to the normal physiology of the wearer; and
      vii. notify the wearer when the current physiology of the wearer deviates from the normal physiology of the wearer.

2. The computerized eyewear of claim 1, wherein the current physiology is a current alertness level of the wearer and the normal physiology is a normal alertness level of the wearer.

3. The computerized eyewear of claim 2, wherein
   a. the one or more sensors comprises an accelerometer;
   b. the computerized eyewear is further configured to:
      i. receive a signal from the accelerometer;
      ii. determine a current head position of the wearer at least partially based on the received signal from the accelerometer; and
      iii. compare the current head position of the wearer to a baseline head position of the wearer.

4. The computerized eyewear of claim 2, wherein
   a. the one or more sensors comprises a pulse oximeter;
   b. the computerized eyewear is further configured to:
      i. receive a signal from the pulse oximeter;
      ii. determine a current oxygen level of the wearer at least partially based on the received signal from the pulse oximeter; and
      iii. compare the current oxygen level of the wearer to a baseline oxygen level of the wearer.

5. The computerized eyewear of claim 4, wherein
   a. the one or more sensors further comprises a camera;
   b. the computerized eyewear is further configured to:
      i. capture at least one image by the camera;
      ii. at least partially in response to capturing the at least one image, analyzing the at least one image to determine a current head position of the wearer;
      iii. compare the current head position of the wearer to a baseline head position of the wearer;
      iv. at least partially in response to comparing (a) the current oxygen level of the wearer to the base line oxygen level of the wear, and (b) the current head position of the wearer to the baseline head position of the wearer, determining the current alertness level of the wearer; and
      v. notifying the wearer of the wearer's current alertness level.

6. The computerized eyewear of claim 4, wherein
   a. the one or more sensors further comprises an eye-facing camera; and
   b. the computerized eyewear is further configured to:
      i. capture at least one image by the eye-facing camera;
      ii. at least partially in response to capturing the at least one image, analyze the at least one image to determine a current pupil size of the wearer;
      iii. compare the current pupil size of the wearer to a baseline pupil size of the wearer;
      iv. at least partially in response to comparing (a) the current oxygen level of the wearer to the baseline oxygen level of the wear, and (b) the current pupil size of the wearer to the baseline pupil size of the wearer, determining the current alertness level of the wearer; and
      v. notify the wearer of the wearer's current alertness level.

7. The computerized eyewear of claim 2, wherein
a. the one or more sensors comprises a gyroscope; and
b. the computerized eyewear is further configured to:
   i. receive one or more signals from the gyroscope;
   ii. determine a current pitch, roll, and yaw of the wearer's head at least partially based on the received one or more signals from the gyroscope; and
   iii. compare the current pitch, roll, and/or yaw of the wearer's head to a baseline pitch, roll, and/or yaw of the wearer's head.

8. The computerized eyewear of claim 7, wherein the computerized eyewear is further configured to determine the current posture of the wearer at least partially based on the current pitch, roll, and yaw of the wearer's head.

9. The computerized eyewear of claim 8, wherein the computerized eyewear is further configured to notify the wearer when the current pitch, roll, and/or yaw deviates from the baseline pitch, roll, and yaw by a predetermined amount.

10. The computerized eyewear of claim 9, wherein
a. the one or more sensors further comprises a pulse oximeter; and
b. the computerized eyewear is further configured to:
   i. receive a signal from the pulse oximeter;
   ii. determine a current oxygen level of the wearer at least partially based on the received signal from the pulse oximeter;
   iii. compare the current oxygen level of the wearer to a baseline oxygen level of the wearer; and
   iv. determine an alertness level of the wearer at least partially based on the current pitch, roll, and/or yaw of the wearer's head and the current oxygen level of the wearer.

11. The computerized eyewear of claim 2, wherein
a. the one or more sensors further comprises a blink rate sensor; and
b. the computerized eyewear is further configured to:
   i. receive a signal from the blink rate sensor;
   ii. determine a current blink rate of the wearer at least partially based on the received signal from the blink rate sensor;
   iii. compare the current blink rate of the wearer to a baseline blink rate of the wearer;
   iv. determine whether the blink rate is below a particular blink rate threshold value; and
   v. at least partially in response to determining that the blink rate is below the particular blink rate threshold value, convey an alert to the wearer or other individual.

12. A computerized eyewear comprising:
a. a frame;
b. one or more temples coupled to the frame;
c. at least one processor operatively coupled to one of the frame or the one or more temples;
d. memory operatively coupled to the at least one processor;
e. one or more sensors operatively coupled to the at least one processor and at least partially embedded in one of the frame or the one or more temples, the one or more sensors selected from the group consisting of:
   i. a gyroscope,
   ii. an accelerometer,
   iii. a geomagnetic sensor,
   iv. a pulse oximeter,
   v. a forward facing camera, and
   vi. an eye-facing camera;
f. a power source operatively coupled to the at least one processor; and
g. a communication device operatively coupled to the at least one processor;
wherein the computerized eyewear is configured to:
   i. determine a baseline physiology of the wearer;
   ii. store the baseline physiology in memory;
   iii. determine a normal physiology of the wearer based on the baseline physiology;
   iv. receive at least one signal from the one or more sensors on the computerized wearable device;
   v. at least partially in response to receiving the at least one signal, determine a current physiology of the wearer of the computerized eyewear;
   vi. at least partially in response to determining the current physiology of the wearer, compare the current physiology of the wearer to the normal physiology of the wearer; and
   vii. notify the wearer when the current physiology of the wearer differs from the normal physiology of the wearer.

13. The computerized eyewear of claim 12, wherein:
a. the one or more sensors comprises an eye-facing camera; and
b. the determining a current physiology of the wearer of the computerized eyewear further comprises:
   i. capturing one or more images by the eye-facing camera;
   ii. at least partially in response to capturing the one or more images, analyzing the one or more images to determine a current eye physiology of the wearer; and
   iii. comparing the current eye physiology to the normal physiology of the wearer.

14. The computerized eyewear of claim 13, wherein the difference between the current eye physiology and the normal physiology indicates that the wearer sustained a concussion.

15. The computerized eyewear of claim 13, wherein the current eye physiology is one or more eye characteristics selected from a group consisting of:
a. pupil size;
b. eye movement; and
c. eye position.

16. The computerized eyewear of claim 13, wherein a current alertness of the wearer is at least partially determined based on a difference between the current eye physiology and the normal physiology.

17. The computerized eyewear of claim 12, wherein:
a. the one or more sensors comprises an accelerometer; and
b. the computerized eyewear is further configured to:
   i. receive a signal from the accelerometer;
   ii. determine a current head position of the wearer at least partially based on the received signal from the accelerometer; and
   iii. compare the current head position of the wearer to the normal physiology of the wearer.

18. The computerized eyewear of claim 12, wherein:
a. the one or more sensors comprises a pulse oximeter;
b. the step of determining a current physiology of the wearer of the computerized eyewear further comprises determining a current oxygen level of the wearer at least partially based on the received signal; and c. the step of comparing the current physiology of the wearer to the baseline physiology of the wearer further comprises comparing the current oxygen level to the normal physiology.

* * * * *

UNITED STATES PATENT AND TRADEMARK OFFICE
CERTIFICATE OF CORRECTION

PATENT NO. : 10,307,085 B2  
APPLICATION NO. : 14/610439  
DATED : June 4, 2019  
INVENTOR(S) : Jay William Sales et al.

It is certified that error appears in the above-identified patent and that said Letters Patent is hereby corrected as shown below:

On the Title Page

Page 4, Column 2 In Other References, "Bhankland, Stephen" should read --Shankland, Stephen--.

Page 5, Column 2 In Other References, "Office Action, dated Mar. 2, 2018, from corresponding U.S. Appl. No. 15/060,333" should read --Final Office Action, dated Mar. 2, 2018, from corresponding U.S. Appl. No. 15/060,333--.

In the Claims

In Claim 1, Column 21 Line 56, "at first time" should read --at a first time--.

Signed and Sealed this  
Twenty-second Day of October, 2019

Andrei Iancu  
*Director of the United States Patent and Trademark Office*